(12) United States Patent
Sakaguchi

(10) Patent No.: US 8,934,604 B2
(45) Date of Patent: Jan. 13, 2015

(54) IMAGE DISPLAY APPARATUS AND X-RAY DIAGNOSTIC APPARATUS

(75) Inventor: Takuya Sakaguchi, Shioya-gun (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 775 days.

(21) Appl. No.: 12/237,675

(22) Filed: Sep. 25, 2008

(65) Prior Publication Data
US 2009/0086912 A1    Apr. 2, 2009

(30) Foreign Application Priority Data

Sep. 28, 2007  (JP) ................................. 2007-256339
Sep. 28, 2007  (JP) ................................. 2007-256340

(51) Int. Cl.
*A61B 6/02*   (2006.01)
*A61B 6/03*   (2006.01)
*A61B 6/00*   (2006.01)
*A61B 5/02*   (2006.01)

(52) U.S. Cl.
CPC .............. *A61B 6/032* (2013.01); *A61B 6/5211* (2013.01); *A61B 6/461* (2013.01); *A61B 5/02007* (2013.01); *A61B 6/4441* (2013.01)
USPC .......................................... 378/62; 378/98.8

(58) Field of Classification Search
CPC ............................. A61B 6/461; A61B 6/5211
USPC ................. 382/132; 378/4, 62, 98.8
See application file for complete search history.

(56) References Cited

U.S. PATENT DOCUMENTS

| 4,624,007 | A | * | 11/1986 | Muranushi ......................... 378/4 |
| 4,920,573 | A | * | 4/1990 | Rhodes et al. ................. 382/131 |
| 5,117,829 | A | * | 6/1992 | Miller et al. ................... 600/427 |
| 5,285,786 | A | * | 2/1994 | Fujii .............................. 600/425 |
| 5,289,373 | A | * | 2/1994 | Zarge et al. .................... 600/434 |
| 5,371,778 | A | * | 12/1994 | Yanof et al. ........................ 378/4 |
| 5,699,799 | A | * | 12/1997 | Xu et al. ......................... 600/407 |
| 5,883,933 | A | * | 3/1999 | Goto et al. ....................... 378/62 |
| 5,891,030 | A | * | 4/1999 | Johnson et al. ............... 600/407 |
| 6,047,080 | A | * | 4/2000 | Chen et al. ..................... 382/128 |
| 6,108,573 | A | * | 8/2000 | Debbins et al. ............... 600/410 |

(Continued)

FOREIGN PATENT DOCUMENTS

| JP | 8-332191 A | 12/1996 |
| JP | 2000-84095 | 3/2000 |

(Continued)

OTHER PUBLICATIONS

Japanese Office Action mailed on May 8, 2012, issued for JP Application No. 2007-256339.

(Continued)

*Primary Examiner* — Thomas R Artman
(74) *Attorney, Agent, or Firm* — Oblon, Spivak, McClelland, Maier & Neustadt, L.L.P.

(57) ABSTRACT

In an image display apparatus of this invention, an image creation unit creates a plurality of cross-sectional images and a projected image from the volume data acquired at a CT volume data acquisition unit. The plurality of cross-sectional images and projected image are displayed on a monitor. When a specific point on the plurality of cross-sectional images displayed on the monitor is clicked at an operation unit, a line is displayed on the projected image displayed on the monitor according to the click.

13 Claims, 25 Drawing Sheets

(56) References Cited

U.S. PATENT DOCUMENTS

| | | | |
|---|---|---|---|
| 6,529,758 B2* | 3/2003 | Shahidi | 600/407 |
| 6,591,130 B2* | 7/2003 | Shahidi | 600/424 |
| 6,674,833 B2* | 1/2004 | Shahidi et al. | 378/4 |
| 6,711,433 B1* | 3/2004 | Geiger et al. | 600/431 |
| 6,782,284 B1* | 8/2004 | Subramanyan et al. | 600/407 |
| 6,792,066 B1* | 9/2004 | Harder et al. | 378/4 |
| 6,807,292 B1* | 10/2004 | Goto et al. | 382/128 |
| 6,842,638 B1* | 1/2005 | Suri et al. | 600/425 |
| 6,865,286 B2* | 3/2005 | Florent et al. | 382/128 |
| 6,891,963 B1* | 5/2005 | Goto et al. | 382/131 |
| 7,333,648 B2* | 2/2008 | Edic et al. | 382/131 |
| 7,424,140 B2* | 9/2008 | Matsumoto | 382/128 |
| 7,463,262 B2* | 12/2008 | Ema | 345/427 |
| 7,496,222 B2* | 2/2009 | Mussack et al. | 382/131 |
| 7,551,761 B2* | 6/2009 | Geiger et al. | 382/128 |
| 7,639,855 B2* | 12/2009 | Matsumoto | 382/131 |
| 7,668,285 B2* | 2/2010 | Mukumoto | 378/4 |
| 7,786,990 B2* | 8/2010 | Wegenkittl et al. | 345/419 |
| 7,844,320 B2* | 11/2010 | Shahidi | 600/424 |
| 7,970,193 B2* | 6/2011 | Rouet et al. | 382/131 |
| 8,086,013 B2* | 12/2011 | Wang | 382/132 |
| 8,116,848 B2* | 2/2012 | Shahidi | 600/424 |
| 8,577,444 B2* | 11/2013 | Klingenbeck-Regn et al. | 600/424 |
| 2002/0106116 A1* | 8/2002 | Knoplioch et al. | 382/128 |
| 2002/0118869 A1* | 8/2002 | Knoplioch et al. | 382/131 |
| 2003/0032878 A1* | 2/2003 | Shahidi | 600/429 |
| 2003/0053697 A1* | 3/2003 | Aylward et al. | 382/203 |
| 2003/0108145 A1* | 6/2003 | Knoplioch et al. | 378/4 |
| 2004/0220466 A1* | 11/2004 | Matsumoto | 600/407 |
| 2004/0223636 A1* | 11/2004 | Edic et al. | 382/131 |
| 2004/0249270 A1* | 12/2004 | Kondo et al. | 600/425 |
| 2005/0185831 A1* | 8/2005 | Rasche et al. | 382/133 |
| 2006/0159326 A1* | 7/2006 | Rasche et al. | 382/131 |
| 2006/0229513 A1* | 10/2006 | Wakai | 600/407 |
| 2006/0250386 A1* | 11/2006 | Movassaghi et al. | 345/419 |
| 2007/0053478 A1* | 3/2007 | Tsuyuki et al. | 378/4 |
| 2009/0010520 A1* | 1/2009 | Wang | 382/132 |
| 2009/0086912 A1* | 4/2009 | Sakaguchi | 378/98.5 |

FOREIGN PATENT DOCUMENTS

| | | |
|---|---|---|
| JP | 2002-119502 A | 4/2002 |
| JP | 2003-33349 | 2/2003 |
| JP | 2004-329729 A | 11/2004 |
| JP | 2005-198708 | 7/2005 |
| JP | 2006-126 | 1/2006 |
| JP | 2006-305203 | 11/2006 |
| JP | 2007-6913 A | 1/2007 |
| JP | 2007-136184 | 6/2007 |
| JP | 2007-530122 A | 11/2007 |
| JP | 2009-82471 A | 4/2009 |
| JP | 2012-205921 A | 10/2012 |

OTHER PUBLICATIONS

Japanese Office Action mailed on May 8, 2012, issued for JP Application No. 2007-256340.

Japanese Office Action issued Dec. 11, 2012 in Patent Application No. 2012-154127 with English Translation.

Japanese Office Action issued Dec. 11, 2012 in Patent Application No. 2007-256339 with English Translation.

Japanese Office Action issued Dec. 11, 2012 in Patent Application No. 2007-256340 with English Translation.

* cited by examiner

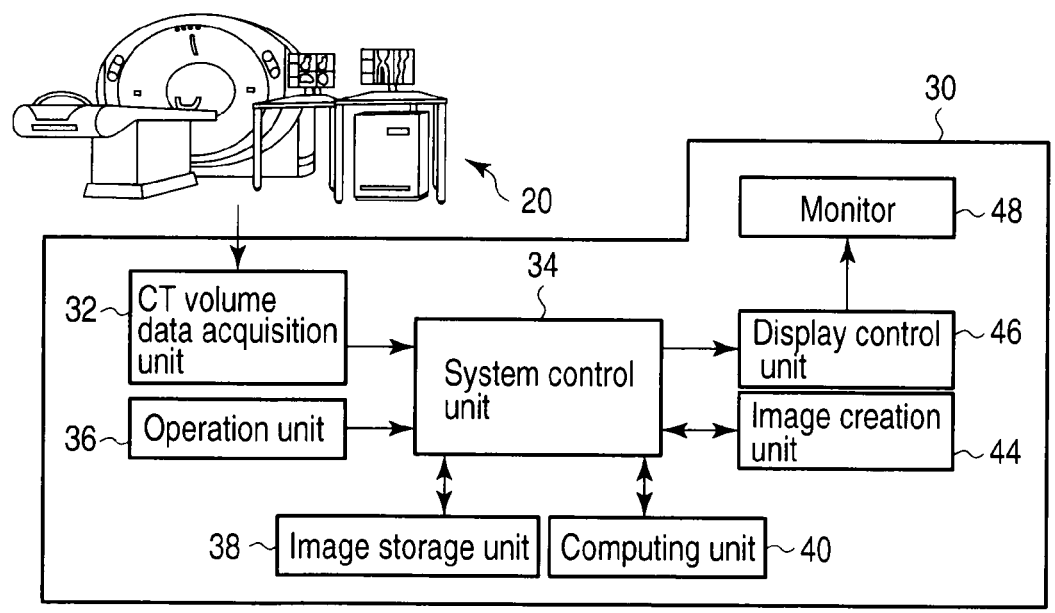
F I G. 2 A

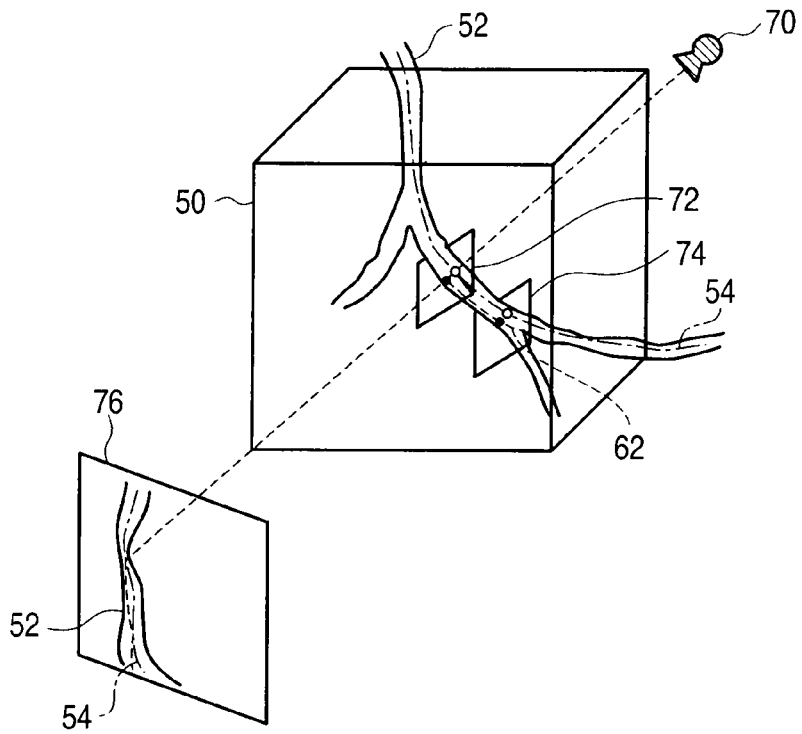
F I G. 6
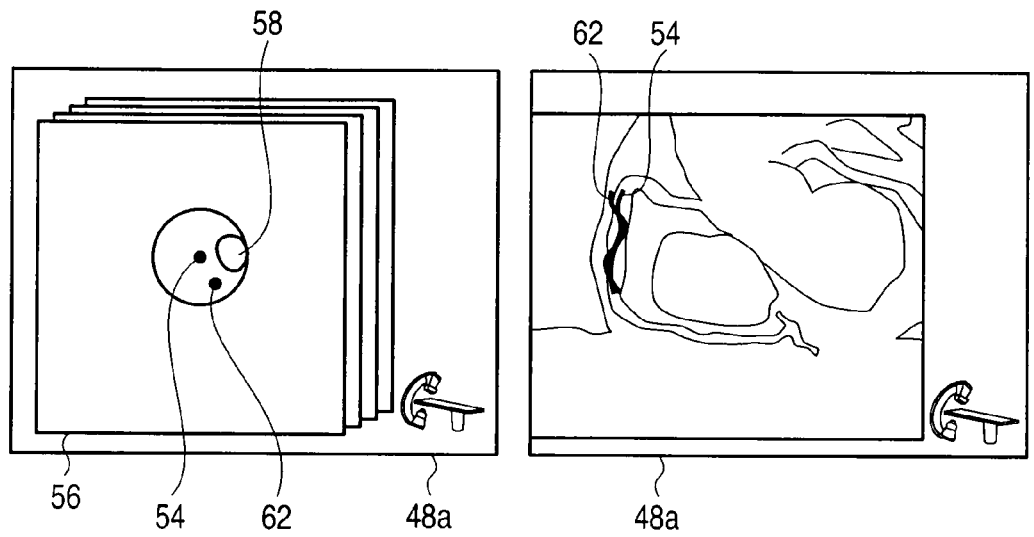
F I G. 7A  F I G. 7B

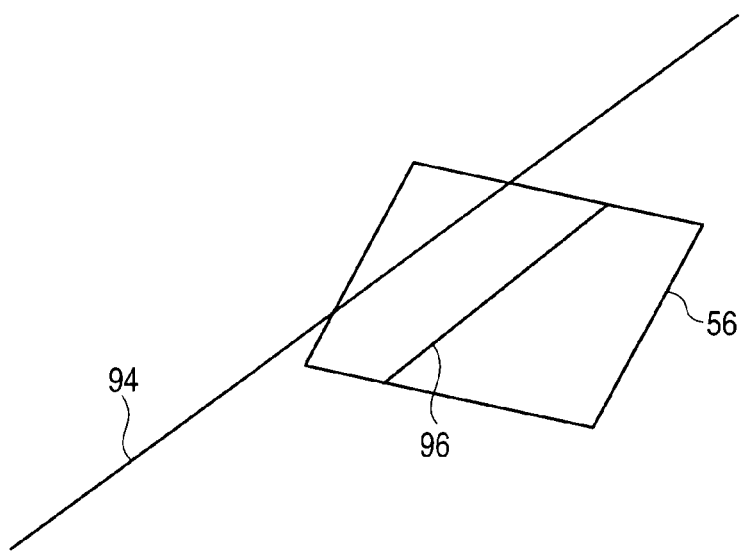
F I G. 20
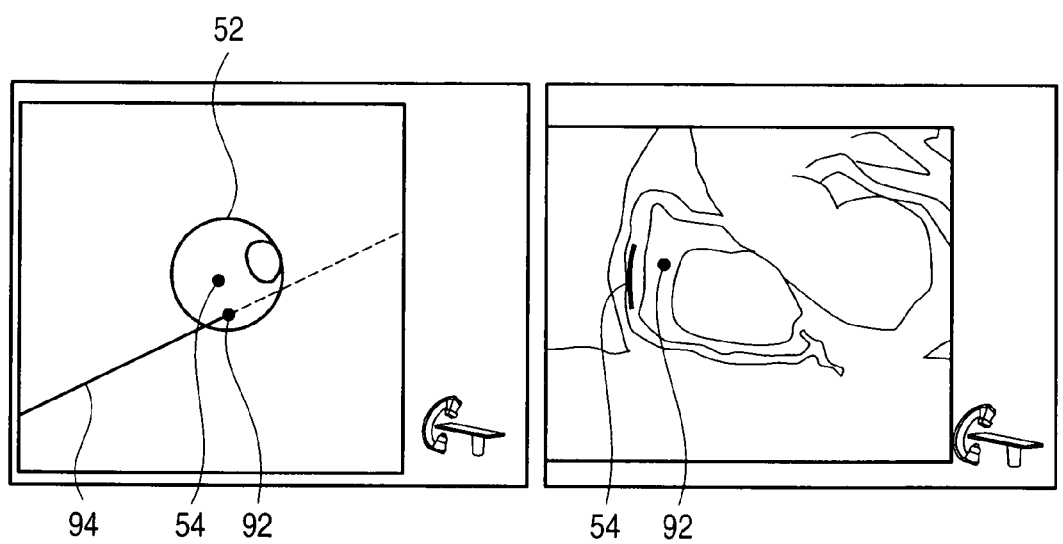
F I G. 21 A   F I G. 21 B

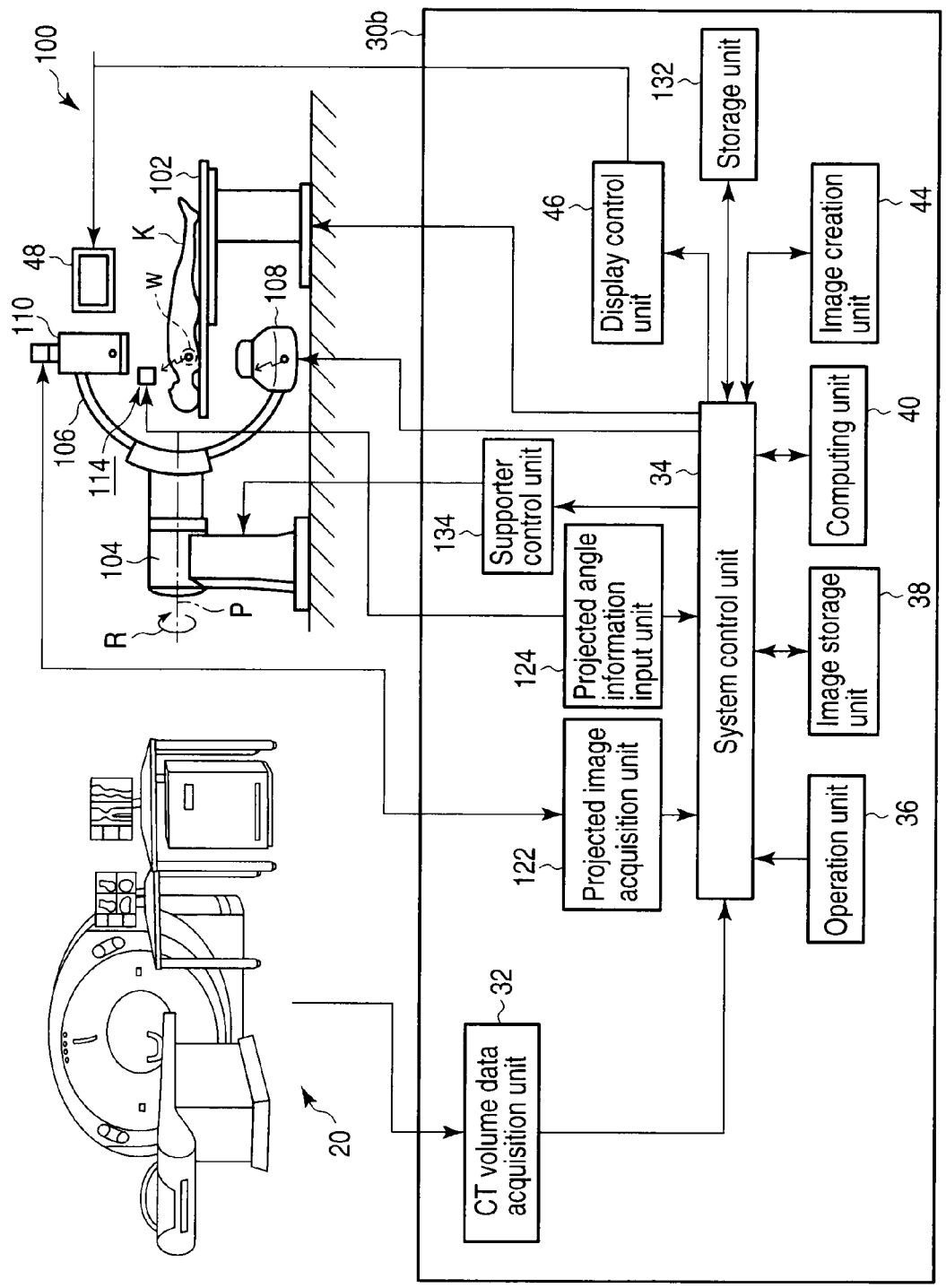
F I G. 23

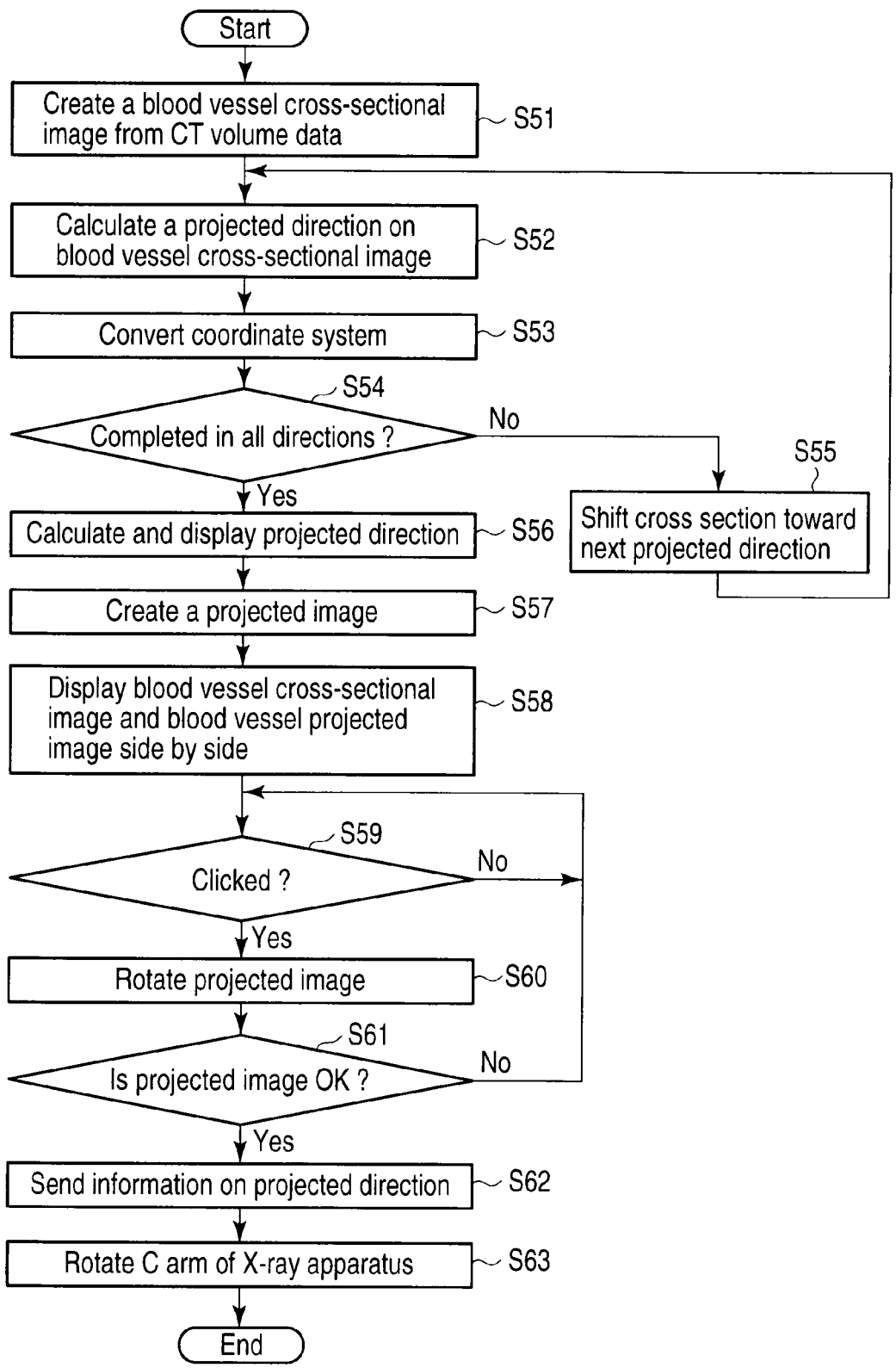
F I G. 2 4

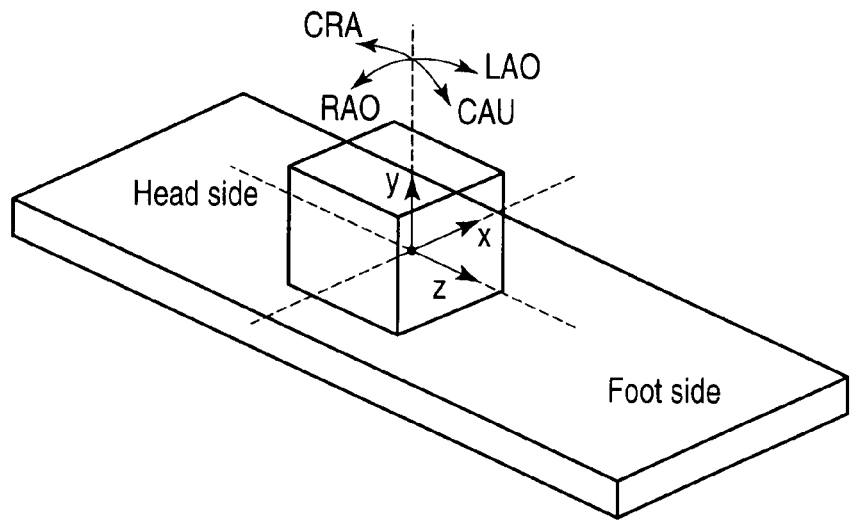
F I G. 27
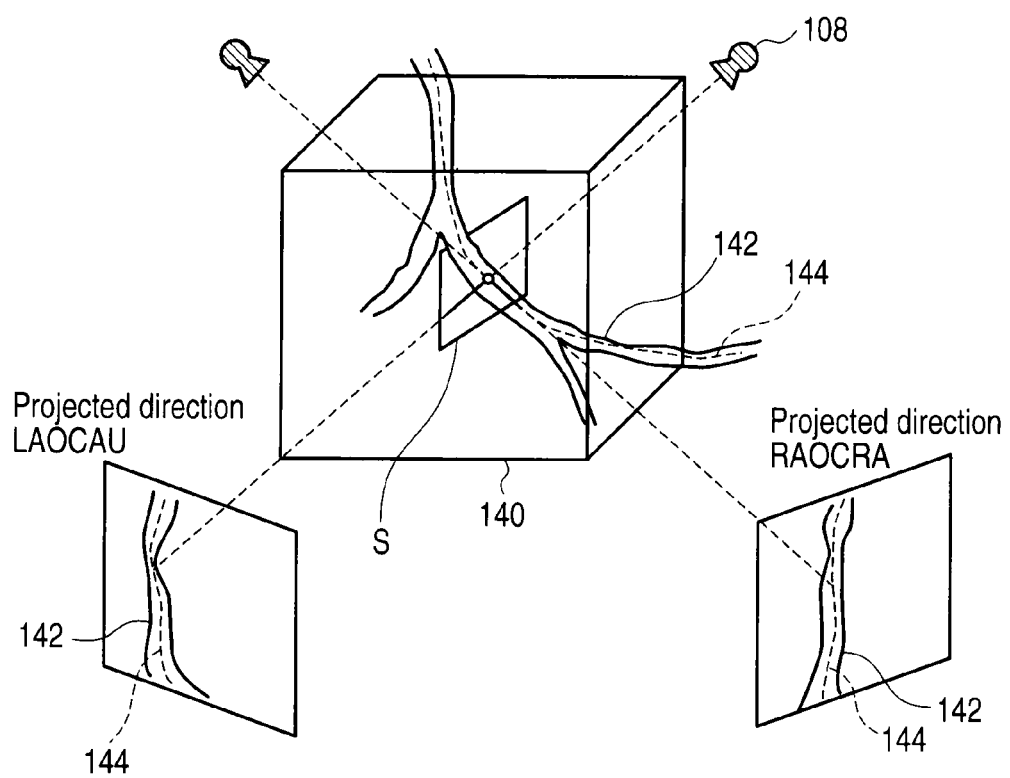
F I G. 28

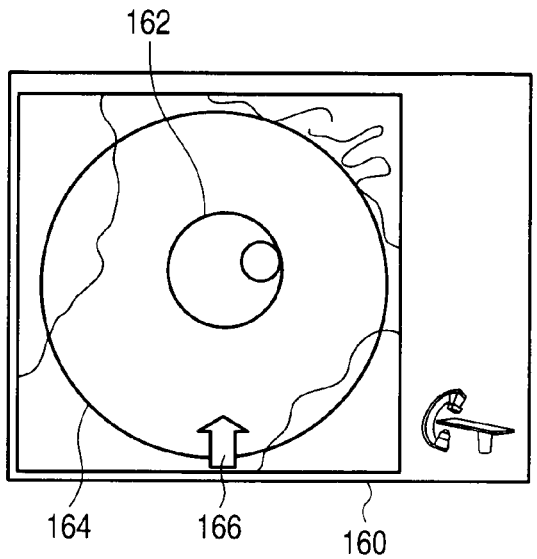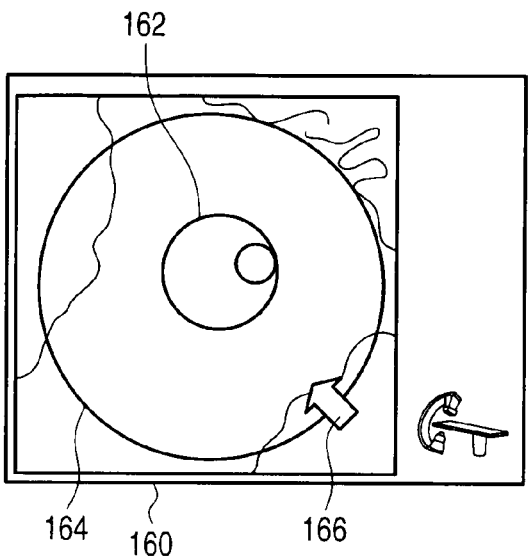
FIG. 32A  FIG. 32B
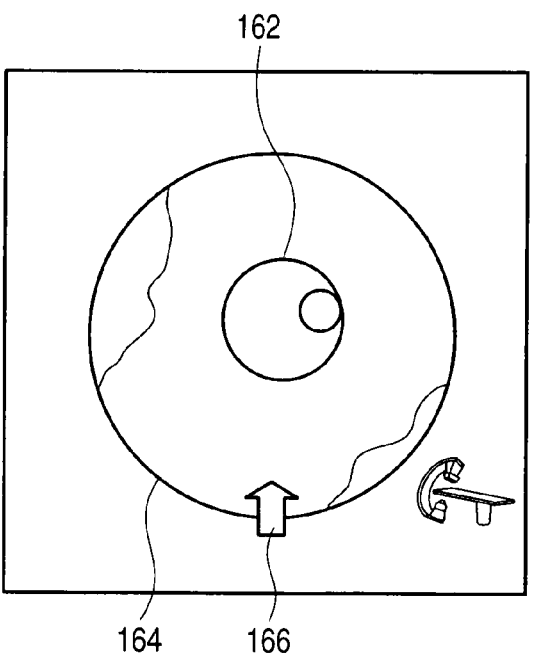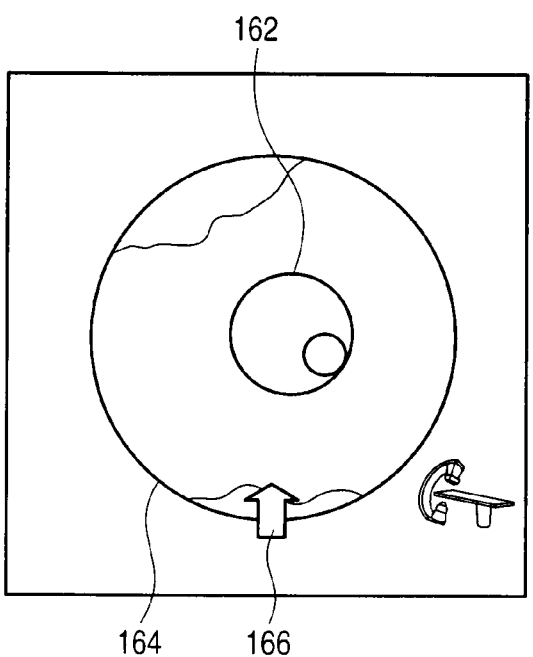
FIG. 33A  FIG. 33B

IMAGE DISPLAY APPARATUS AND X-RAY DIAGNOSTIC APPARATUS

CROSS-REFERENCE TO RELATED APPLICATIONS

This application is based upon and claims the benefit of priority from prior Japanese Patent Applications No. 2007-256339, filed Sep. 28, 2007; and No. 2007-256340, filed Sep. 28, 2007, the entire contents of both of which are incorporated herein by reference.

BACKGROUND OF THE INVENTION

1. Field of the Invention

This invention relates to an image display apparatus and an X-ray diagnostic apparatus, and more particularly to an improvement in an endovascular treatment method, especially an improvement in a method of drawing a wire route projected line for passing through a complete obstruction and determining an observation direction in endovascular treatment.

2. Description of the Related Art

There has been an endovascular treatment method. In recent years, the endovascular treatment method has suddenly been popularized since such a device as a guide wire (hereinafter, referred to as a wire) or a catheter is inserted into a blood vessel and moved forward to treat the affected area with the device, which makes the method less invasive than and as effective as an abdominal operation. In the future, use of computed tomography images (CT images) will become mainstream in developing a treatment plan.

Computed tomography (CT) images are volume (3D) data obtained by taking images and reconstructing the images with a CT scanner which collects X-ray projected images through an angle of 360 degrees around the human body and reconstructs the images into two-dimensional tomographic images. The volume data enables a cross-sectional image of a blood vessel to be observed and therefore is very useful.

For example, in a treatment for a complete obstruction where a blood vessel is clogged completely, the operator creates blood vessel cross-sectional images 2 from the CT volume data as shown in FIG. 1. In the blood vessel cross-sectional images 2, the operator observes a hard part (such as a calcified part) 6 and a soft part (such as a soft plaque) 8 in the clogged part of a blood vessel 4 and determines on which side of the blood vessel 4 the wire should be moved forward. From FIG. 1, it is seen that a fibrotic part 12 on the left side of the vessel center line 10 is a part through which the wire is easily passed. One publicly-known document is, for example, Morton J. Kern, "Cardiac Catheterization Handbook" Igaku-Shoin Ltd.

When the operator who has developed a treatment plan using the aforementioned blood vessel cross-sectional images enters a catheter room for actual treatment, images obtained in real time from the X-ray imaging system in the catheter room are blood vessel projected images, not blood vessel cross-sectional images. For this reason, the operator has to convert the three-dimensional positional relationship between the currently seen projected image and the planned cross-sectional images in the operator's head and convert the treatment plan from the planned blood vessel cross-sectional images into the blood vessel projected image right in front of the operator's eyes.

However, the conversion work in the operator's head is a great burden on the operator, particularly when the operator is still a bit new. There is a risk of a new operator being irresolute or making a mistake.

BRIEF SUMMARY OF THE INVENTION

It is, accordingly, an object of the invention to provide an image display apparatus and an X-ray diagnostic apparatus which are capable of making three-dimensional positional relationship, particularly the relationship between blood vessel cross-sectional images and a blood vessel projected image, easier to understand and displaying the easier-to-understand relationship.

According to an aspect of the invention, there is provided an image display apparatus comprising: a volume data acquisition unit which acquires volume data; a cross-sectional image creation unit which creates a cross-sectional images from the volume data acquired by the volume data acquisition unit; a projected image creation unit which creates a projected image; a display unit which displays the cross-sectional images and the projected image; a specification unit which specifies a specific point on the cross-sectional images displayed on the display unit; and a control unit which, according to the specific point specified by the specification unit, displays a point on the projected image displayed on the display unit.

According to another aspect of the invention, there is provided an image display apparatus comprising: a volume data acquisition unit which acquires volume data; a cross-sectional image creation unit which creates a plurality of cross-sectional images from the volume data acquired by the volume data acquisition unit; a projected image creation unit which creates a projected image; a display unit which displays said plurality of cross-sectional images and the projected image; a specification unit which specifies specific points on said plurality of cross-sectional images displayed on the display unit; and a control unit which, according to the specific points specified by the specification unit, displays a line on the projected image displayed on the display unit.

According to still another aspect of the invention, there is provided an image display apparatus comprising: a volume data acquisition unit which acquires volume data; a cross-sectional image creation unit which creates a plurality of cross-sectional images from the volume data acquired by the volume data acquisition unit; a projected image creation unit which creates a projected image; a display unit which displays said plurality of cross-sectional images and the projected image; a specification unit which specifies a specific point on the projected image displayed on the display unit; and a control unit which, according to the specific point specified by the specification unit, displays a line on the cross-sectional image displayed on the display unit.

According to still another aspect of the invention, there is provided an image display apparatus comprising: a volume data acquisition unit which acquires volume data; a cross-sectional image creation unit which creates a cross-sectional image from the volume data acquired by the volume data acquisition unit; and a computing unit which calculates a projected direction in a radiation direction on the cross-sectional image created by the cross-sectional image creation unit.

According to still another aspect of the invention, there is provided an X-ray diagnostic apparatus which has an X-ray source and an X-ray detector positioned by a supporter so as to face each other with a subject sandwiched between them and which performs the image processing of image data obtained by detecting X-rays shed on the subject by the X-ray source and converting the X-rays into an electrical signal and displays an image, the X-ray diagnostic apparatus comprising: a volume data acquisition unit which acquires volume data; a cross-sectional image creation unit which creates a cross-sectional image from the volume data acquired by the volume data acquisition unit; a computing unit which calculates a projected direction in a radiation direction on the cross-sectional image created by the cross-sectional image creation unit; a projected image creation unit which creates a projected image from the volume data acquired by the volume data acquisition unit; a display unit which displays the cross-sectional image and the projected image; a specification unit which specifies a specific point on the cross-sectional image displayed on the display unit; and a supporter control unit which rotates the supporter, wherein the computing unit, when a specific point is specified at the specification unit, calculates a destination position of the supporter so that the X-ray source is positioned in the direction of the specified specific point, and the supporter control unit rotates the supporter in such a manner that the X-ray source is positioned in the destination position calculated by the computing unit.

According to still another aspect of the invention, there is provided an image display apparatus comprising: a volume data acquisition unit which acquires volume data; a cross-sectional image creation unit which creates a cross-sectional image from the volume data acquired by the volume data acquisition unit; a projected image creation unit which creates a projected image from the volume data acquired by the volume data acquisition unit; a display unit which displays the cross-sectional image and the projected image; an image rotation unit which rotates the projected image in a desired direction; and a computing unit which calculates a projected direction of the rotated projected image, wherein the display unit displays the projected direction calculated at the computing unit on the cross-sectional image.

According to still another aspect of the invention, there is provided an X-ray diagnostic apparatus which has an X-ray source and an X-ray detector positioned by a supporter so as to face each other with a subject sandwiched between them and which performs the image processing of image data obtained by detecting X-rays shed on the subject by the X-ray source and converting the X-rays into an electrical signal and displays an image, the X-ray diagnostic apparatus comprising: a volume data acquisition unit which acquires volume data; a cross-sectional image creation unit which creates a cross-sectional image from the volume data acquired by the volume data acquisition unit; a projected image creation unit which creates a projected image from the volume data acquired by the volume data acquisition unit; a display unit which displays the cross-sectional image and the projected image; an image rotation unit which rotates the projected image in a desired direction; and a computing unit which calculates a projected direction of the rotated projected image, wherein the display unit displays the projected direction calculated at the computing unit on the cross-sectional image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL
VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a block diagram showing the configuration of an image display apparatus according to a first embodiment of the invention and FIG. 2B is a block diagram showing the configuration of an image display apparatus according to a fourth embodiment of the invention;

FIG. 6 is a diagram to help explain how to calculate a curve of a planned wire line in the first embodiment;

FIGS. 7A and 7B are diagrams to help explain the relationship between blood vessel cross-sectional images and a projected image in the first embodiment;

FIG. 20 shows the relationship between a projected line and a blood vessel cross-sectional image;

FIGS. 21A and 21B are diagrams to help explain the relationship between a blood vessel cross-sectional image and a projected image in the third embodiment;

FIG. 23 is a block diagram showing the configuration of an image display apparatus according to a fifth embodiment of the invention;

FIG. 24 is a flowchart to help explain the operation of the image display apparatus according to the fifth embodiment;

FIG. 27 is a diagram to help explain the conversion of a coordinate system;

FIG. 28 is a diagram to help explain how to calculate a projected direction in all directions;

FIGS. 32A and 32B are diagrams to help explain a modification of the fifth embodiment, with an example of an arrow representing the radiation direction being turned;

FIGS. 33A and 33B are diagrams to help explain a modification of the fifth embodiment, showing an example of displaying an arrow representing the radiation direction with a cross-sectional image being turned;

DETAILED DESCRIPTION OF THE INVENTION

Figure 1:
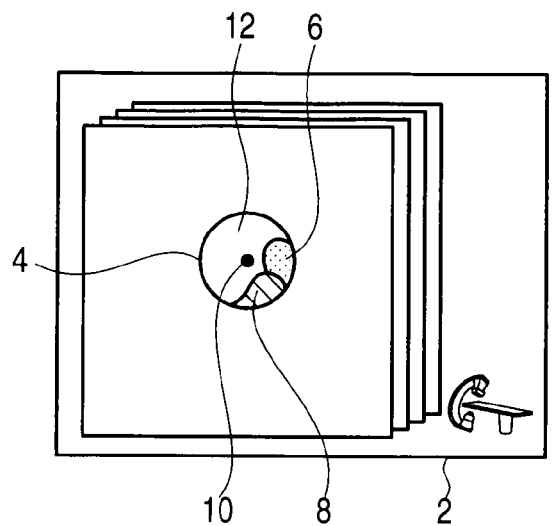
FIG. 1 shows an example of blood vessel cross-sectional images of a complete obstruction.

Hereinafter, referring to the accompanying drawings, embodiments of the invention will be explained.

First Embodiment

FIG. 2A is a block diagram showing the configuration of an image display apparatus according to a first embodiment of the invention.

In FIG. 2A, the image display apparatus 30 comprises a CT volume data acquisition unit 32, a system control unit 34, an operation unit 36, an image storage unit 38, a computing unit 40, an image creation unit 44, a display control unit 46, and a monitor 48.

The CT volume data acquisition unit 32 is for acquiring desired CT volume data from a CT apparatus 20. The system control unit 34 is for supervising the overall control operation of the image display apparatus 30. The operation unit 36, which is composed of a control panel and others, is for clicking a planned wire line on a blood vessel cross section, selecting an image, or the like.

The image storage unit 38 is storage means for storing coordinates and images for the planned wire line. The computing unit 40 is for performing various arithmetical operations, including computing a curve in a 3D image. The image creation unit 44, together with the image storage unit 38, creates images to display them on the monitor 48. The display control unit 46 is for displaying on the monitor 48 a cross-sectional image of the 3D image created by the image storage unit 38 and image creation unit 44. The monitor 48 is for displaying on the screen the 3D image and others output via the display control unit 46.

Next, referring to a flowchart in FIG. 3, the operation of the image display apparatus of the first embodiment will be explained.

Figure 4A:
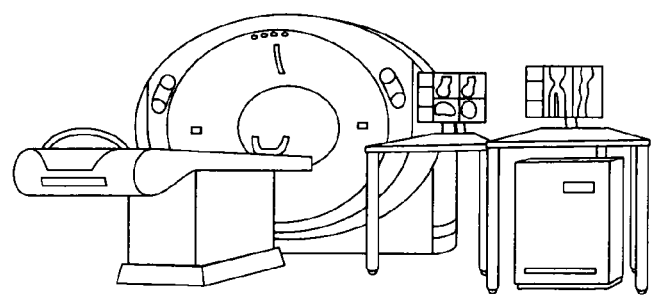
FIGS. 4A to 4C are diagrams to help explain the operation of the image display apparatus of the first embodiment, FIG. 4A showing an example of a CT apparatus, FIG. 4B showing an example of volume data, and FIG. 4C showing an example of a blood vessel cross-sectional image.
Figure 4B:
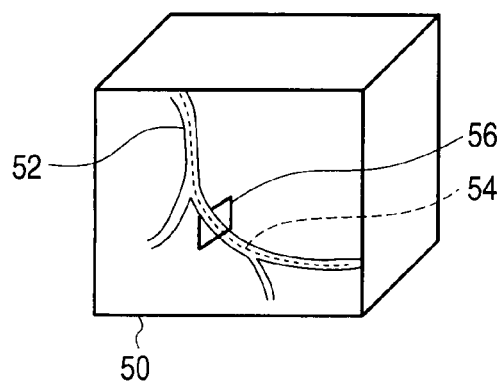
Figure 4C:
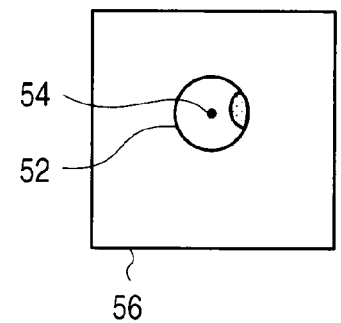

First, in step S1, the CT apparatus 20 creates a blood vessel cross-sectional image from the CT volume data acquired by the CT volume data acquisition unit 32. That is, volume data 50 as shown in FIG. 4B is acquired from the CT apparatus 20 shown in FIG. 4A. Then, the system control unit 34 extracts a blood vessel center line 54 in a blood vessel 52 from the volume data 50. Next, an MPR image perpendicular to the blood vessel center line 54 is created. This is a blood vessel cross-sectional image 56 as shown in FIG. 4C.

Next, in step S2, a projected image is created from the CT volume data 50 obtained in step S1. The operation of creating a projected image is the same as displaying a general CT image.

Figure 5:
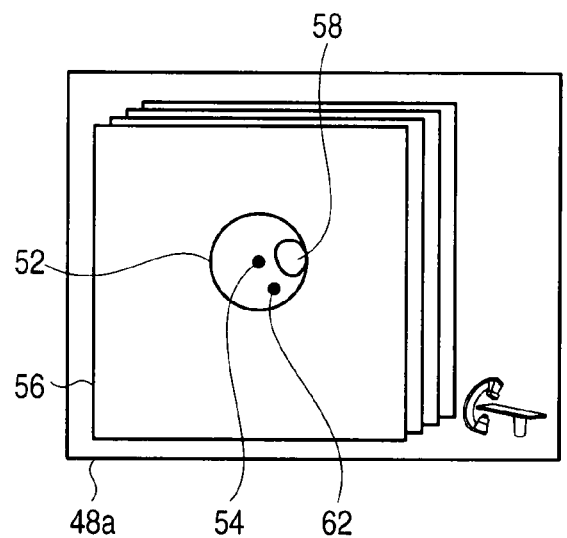
FIG. 5 is a diagram to help explain the operation of the image display apparatus of the first embodiment, showing a plurality of blood vessel cross-sectional images.

In step S3, a planned wire line is clicked on the blood vessel cross-sectional image 56. As shown in FIG. 5, on a plurality of blood vessel cross-sectional images 56, the operator clicks sequentially arbitrary points through which the operator wants to pass the wire. What is obtained by connecting the clicked points consecutively is a planned wire line. In this case, the planned wire line 62 is formed in a part avoiding, for example, a calcified part 58 in the blood vessel 52.

When the planned wire line is formed, a part which is used as a planned wire line is clicked on a blood vessel cross-sectional image 56. Then, in step S4, it is determined whether there is a blood vessel cross-sectional image to be clicked next. Here, if a click has not been completed, control proceeds to step S5, where a blood vessel cross-sectional image adjacent to the first-clicked blood vessel cross-sectional image is displayed on the monitor 48. Then, control proceeds to step S3 again, where another part to be used as a planned wire line is clicked.

In this way, the processing operations in step S3 to step S5 are repeated until the click has been completed in step S4, with the result that a part to function as a planned wire line on an adjacent blood vessel cross-sectional image is clicked. At this time, for example, when the preceding image is clicked, the page is supposed to be turned over and a new adjacent blood vessel cross-sectional image is supposed to be displayed in front of the preceding image. This defines a line in the three-dimensional space and a planned wire line is displayed on a projected image.

Specifically, if the click has been completed in step S4, the blood vessel center line 54 and planned wire line 62 are displayed on the projected image in step S6 as shown in FIG. 6. A point clicked on one cross-sectional image (e.g., 72) has three-dimensional coordinates. Accordingly, if clicking is performed on a plurality of cross-sectional images (e.g., 72, 74), a curve can be calculated in a three-dimensional space where three-dimensional coordinates continue.

Figure 8:
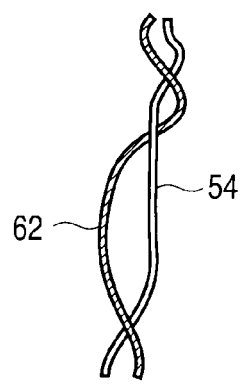
FIG. 8 shows an example of displaying two lines on a projected image.

The calculated curve in the three-dimensional space is projected and drawn on the projected image as shown in FIG. 7B. While looking at a transparent image in the same direction as that of the projected image, the operator operates the wire. When the blood vessel center line 54 and the planned wire line 62 overlap with each other, the two lines are displayed in such a manner that the line closer to the operator's viewpoint preferentially appears above the other line as shown in FIG. 8, taking into account the three-dimensional positional relationship.

When clicking done on a plurality of cross-sectional images, they are not necessarily displayed in such a manner that they are overlapped with one another as shown in FIG. 7A. For example, a plurality of cross-sectional images may be displayed on the screen 48*a* of the monitor 48 at the same time and a desired one may be selected from them.

Figure 9:
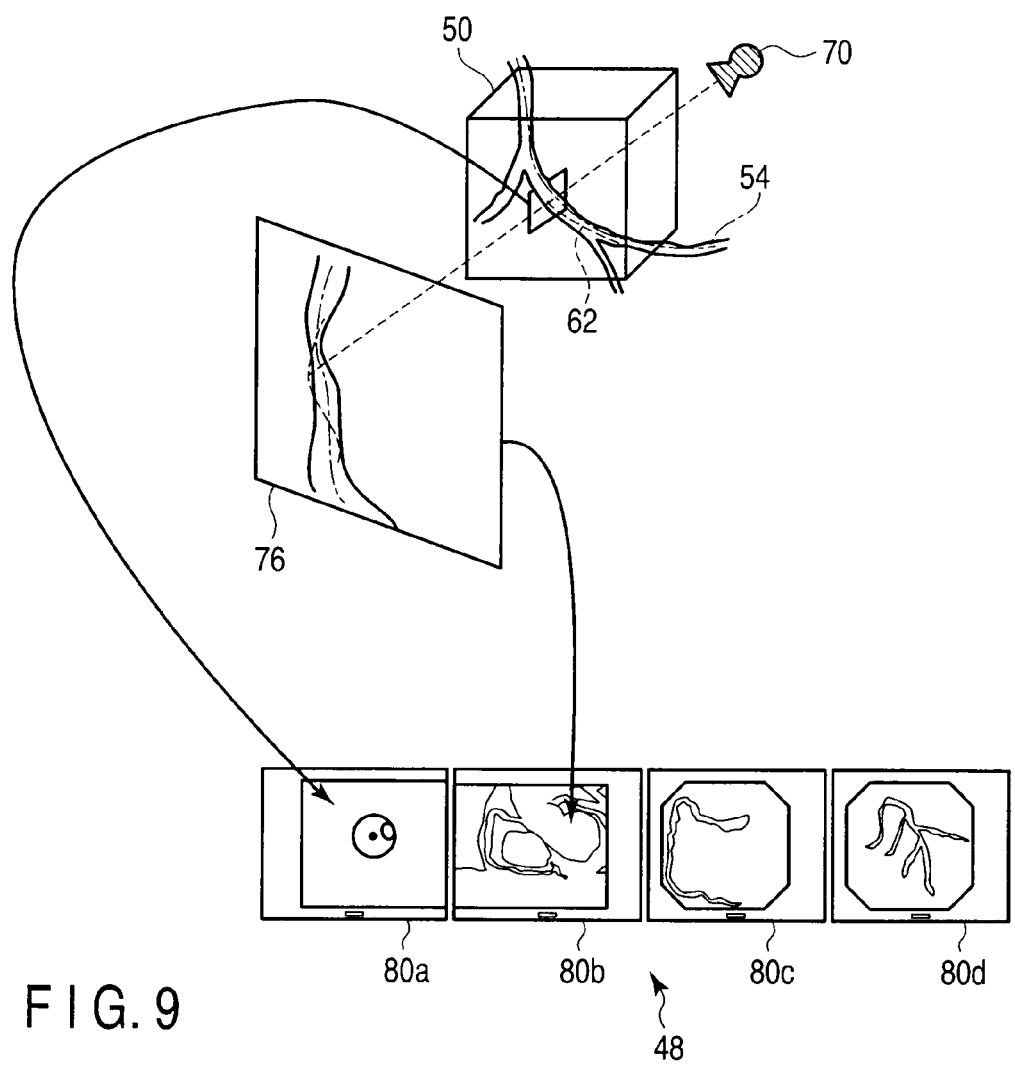
FIG. 9 shows an example of images displayed on a monitor in the first embodiment.

Thereafter, in step S7, the blood vessel cross-sectional image and the blood vessel projected image are displayed side by side on the screen 48*a* of the monitor 48. The blood vessel projected image is not limited to a CT blood vessel projected image. For example, as shown in FIG. 9, a CT blood vessel cross-sectional image 80*a*, and a CT volume rendering (VR) image, maximum intensity projected (MIP), or CathView (a projected image of specific blood vessel slice data) 80*b*, and an X-ray contrast image 80*c*, and a X-ray transparent image 80*d* may be displayed side by side on the screen 48*a* of the monitor 48.

The operation of clicking a part functioning as a planned wire line is performed on the mouse, keyboard, or touch panel in the operation unit 36. A next blood vessel cross-sectional image may be displayed automatically by clicking.

While in the first embodiment, the blood vessel center line and the planned wire line are displayed on the blood vessel projected image, the invention is not restricted to the blood vessel center line and may be applied to any line, provided that the line represents a line connecting at least two arbitrary points including the planned wire line. As for the lines displayed on the blood vessel projected image, for example, if two lines can be distinguished, they may be displayed in different colors, in different line thicknesses, or in different types of lines.

Moreover, near step S4, there may be provided an interface for correcting a wrong click.

In addition, near step S4, a plurality of projected lines may be drawn.

As described above, with the first embodiment, the relationship between a blood vessel cross-sectional image and a blood vessel projected image can be displayed in an easy-to-understand manner.

First Modification of First Embodiment

Next, a first modification of the first embodiment will be explained.

While in the first embodiment, a blood vessel center line and a planned wire line, that is, two lines, are displayed on a blood vessel projected image, the invention is not limited to this. For example, a blood vessel center line and an arbitrary point may be displayed as in the first modification.

Hereinafter, referring to a flowchart in FIG. 10, the operation of an image display apparatus according to the first modification of the first embodiment will be explained.

Figure 10:
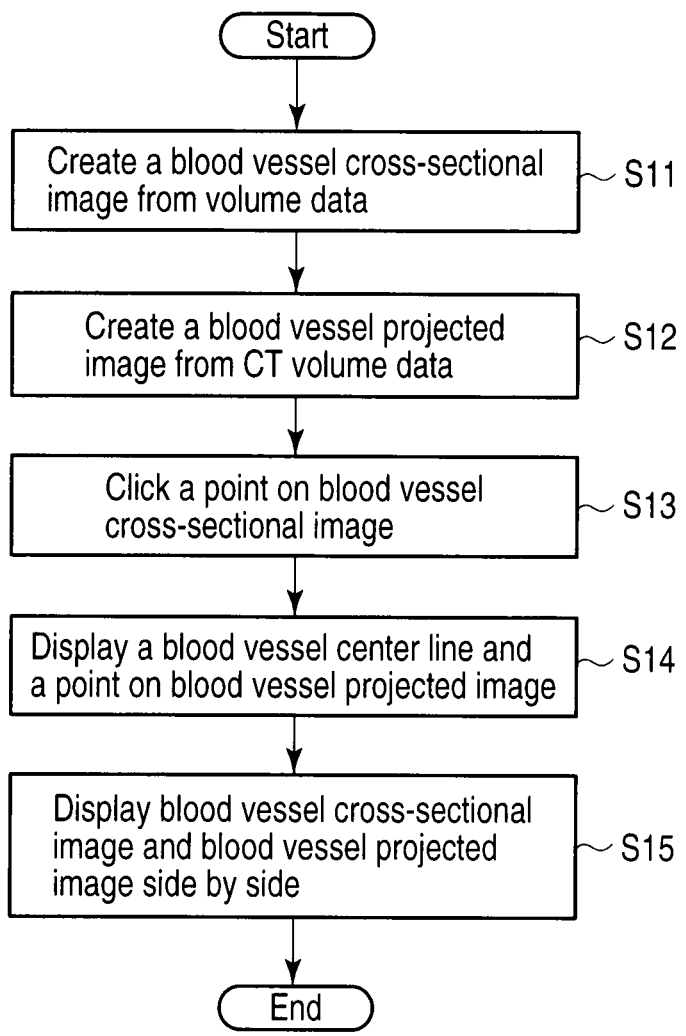
FIG. 10 is a flowchart to help explain the operation of an image display apparatus according to a first modification of the first embodiment.

In the flowchart of FIG. 10, since the operations in steps S11, S12, and S15 are the same as those in steps S1, S2, and S7 of FIG. 3, only steps S13 and S14 differing from FIG. 3 will be explained.

Figures 11A, 11B:
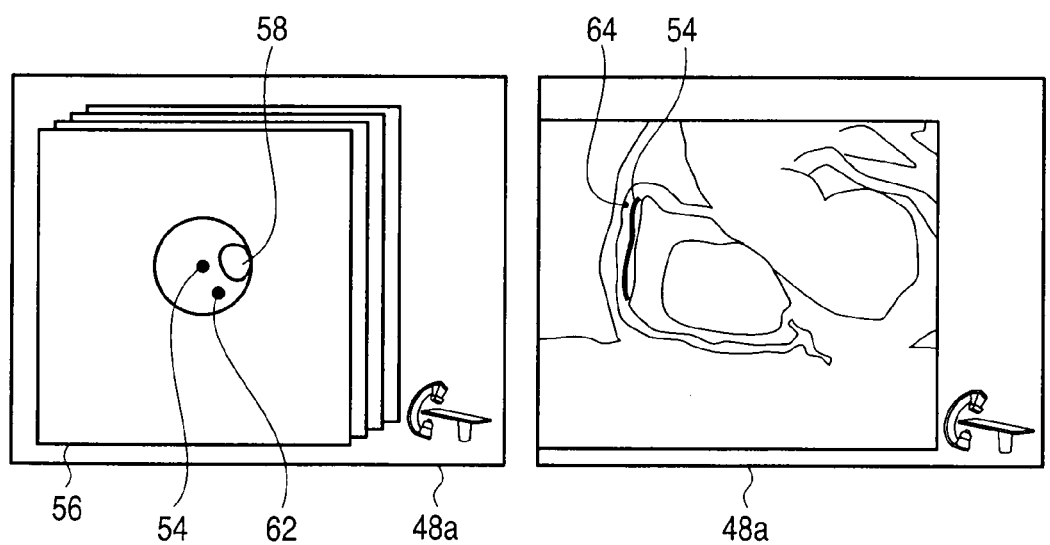
FIGS. 11A and 11B are diagrams to help explain the relationship between blood vessel cross-sectional images and a projected image in the first modification of the first embodiment.

When in steps S11 and S12, a blood vessel cross-sectional image and a projected image are formed, an arbitrary point 64 is clicked on the blood vessel cross-sectional image 56 in step S13 as shown in FIG. 11A. Then, in step S14, a blood vessel center line 54 and the arbitrary point 64 are displayed on the projected image. When clicking is done, the cross-sectional images may be displayed in such a manner that they are overlapped with one another as shown in FIG. 11A.

Since the point clicked on one cross-sectional image has three-dimensional coordinates, the calculated curve in the three-dimensional space is projected and drawn on the projected image as shown in FIG. 11B. Looking at the transparent images in the same direction as that of the projected image, the operator operates the wire. When the blood vessel center line 54 and the point 64 overlap with each other, they are displayed in such a manner that the line closer to the operator's viewpoint preferentially appears above the other line, taking into account the three-dimensional positional relationship.

Thereafter, in step S15, the blood vessel cross-sectional image and the blood vessel projected image are displayed side by side on the screen 48*a* of the monitor 48.

As described above, even with the first modification, use of an arbitrary point representing a relative position with respect to the blood vessel center line makes it possible to display the relationship between the blood vessel cross-sectional image and the blood vessel projected image in an easy-to-understand manner.

Second Modification of First Embodiment

Next, a second modification of the first embodiment will be explained.

While in the first modification of the first embodiment, the blood vessel center line and an arbitrary point are displayed on the blood vessel projected image, an arbitrary point may be clicked, thereby displaying the point as in the second modification.

Hereinafter, referring to a flowchart in FIG. 12, the operation of an image display apparatus according to the second modification of the first embodiment will be explained.

Figure 12:
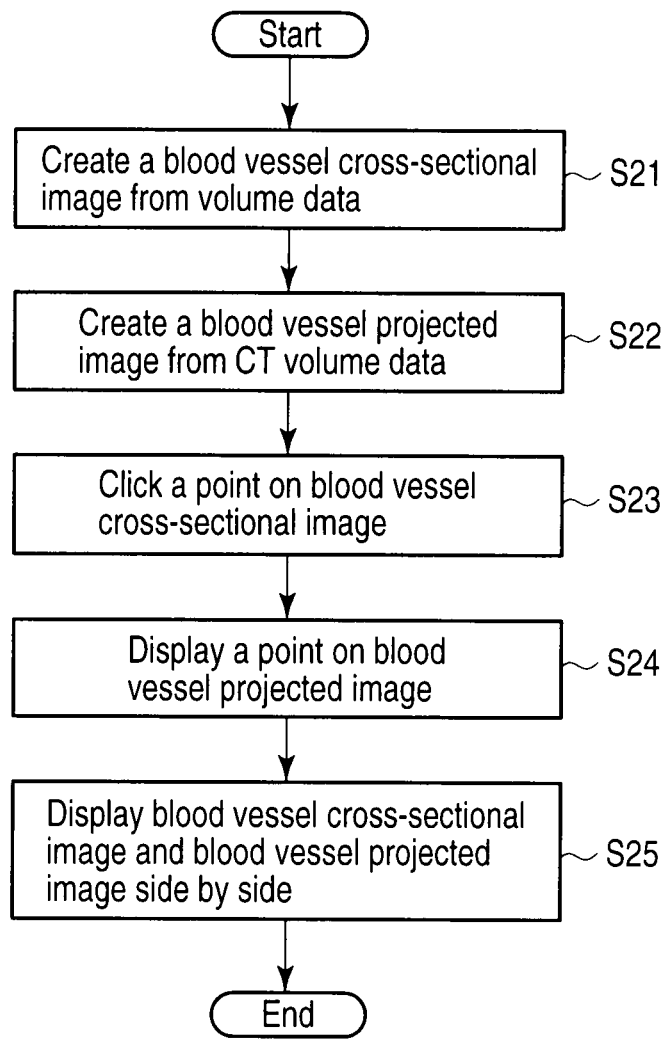
FIG. 12 is a flowchart to help explain the operation of an image display apparatus according to a second modification of the first embodiment.

In the flowchart of FIG. 12, since the operations in steps S21, S22, and S25 are the same as those in steps S1, S2, and S7 of FIG. 3, only steps S23 and S24 differing from FIG. 3 will be explained.

Figure 13A:
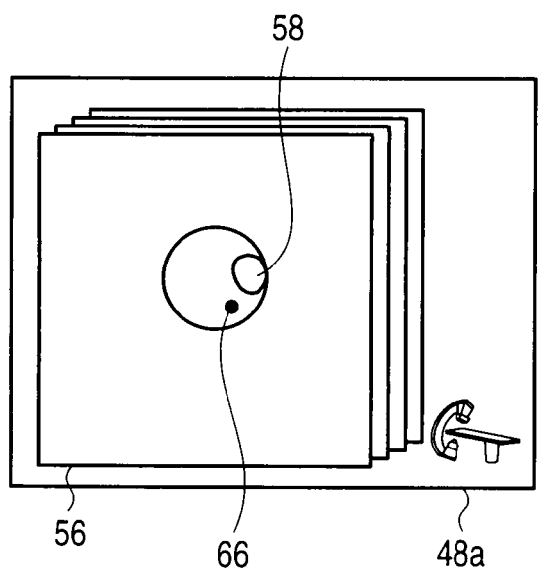
FIGS. 13A and 13B are diagrams to help explain the relationship between blood vessel cross-sectional images and a projected image in the second modification of the first embodiment.

When in steps S21 and S22, a blood vessel cross-sectional image and a projected image are formed, an arbitrary point 66 is clicked on the blood vessel cross-sectional image 56 in step S23 as shown in FIG. 13A. Then, in step S24, the arbitrary point 66 clicked in step S23 is displayed on the projected image.

Figure 13B:
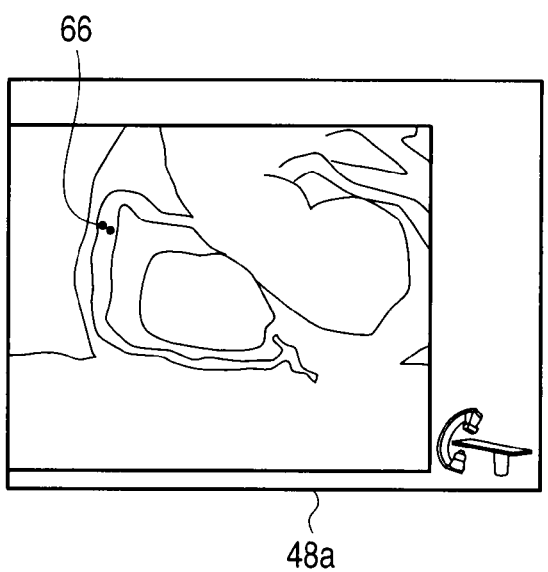

Since the clicked point has three-dimensional coordinates, it is projected in the calculated three-dimensional space and is drawn on the projected image as shown in FIG. 13B. Looking at the transparent images in the same direction as that of the projected image, the operator operates the wire. Thereafter, in step S15, the blood vessel cross-sectional image and the blood vessel projected image are displayed side by side on the screen 48*a* of the monitor 48.

As described above, even with the second modification, the relationship between the blood vessel cross-sectional image and the blood vessel projected image can be displayed in an easy-to-understand manner.

Second Embodiment

Next, a second embodiment of the invention will be explained.

In the first embodiment, clicking on a blood vessel cross-sectional image to form a planned wire line is performed for each of a plurality of cross-sectional images, which is a time-consuming job. To overcome this problem, only a specific blood vessel cross-sectional image is clicked in the second embodiment, thereby improving the time-consuming operation.

Figure 14:
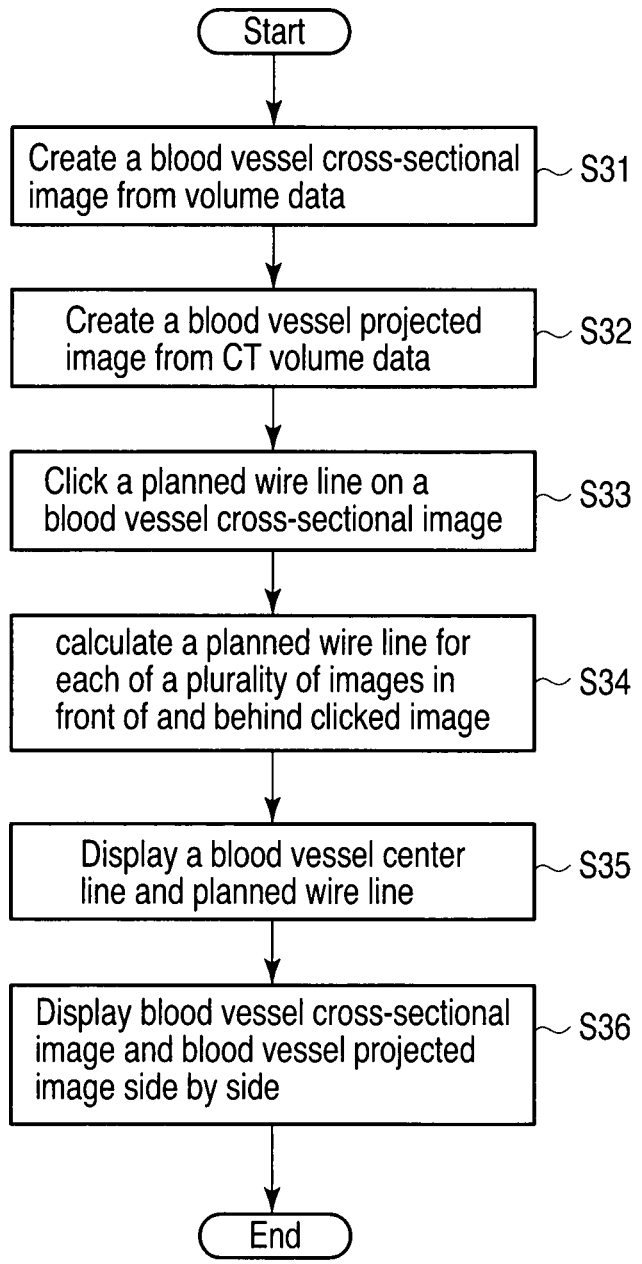
FIG. 14 is a flowchart to help explain the operation of an image display apparatus according to a second embodiment of the invention.

FIG. 14 is a flowchart to help explain the operation of an image display apparatus according to the second embodiment.

Figure 3:
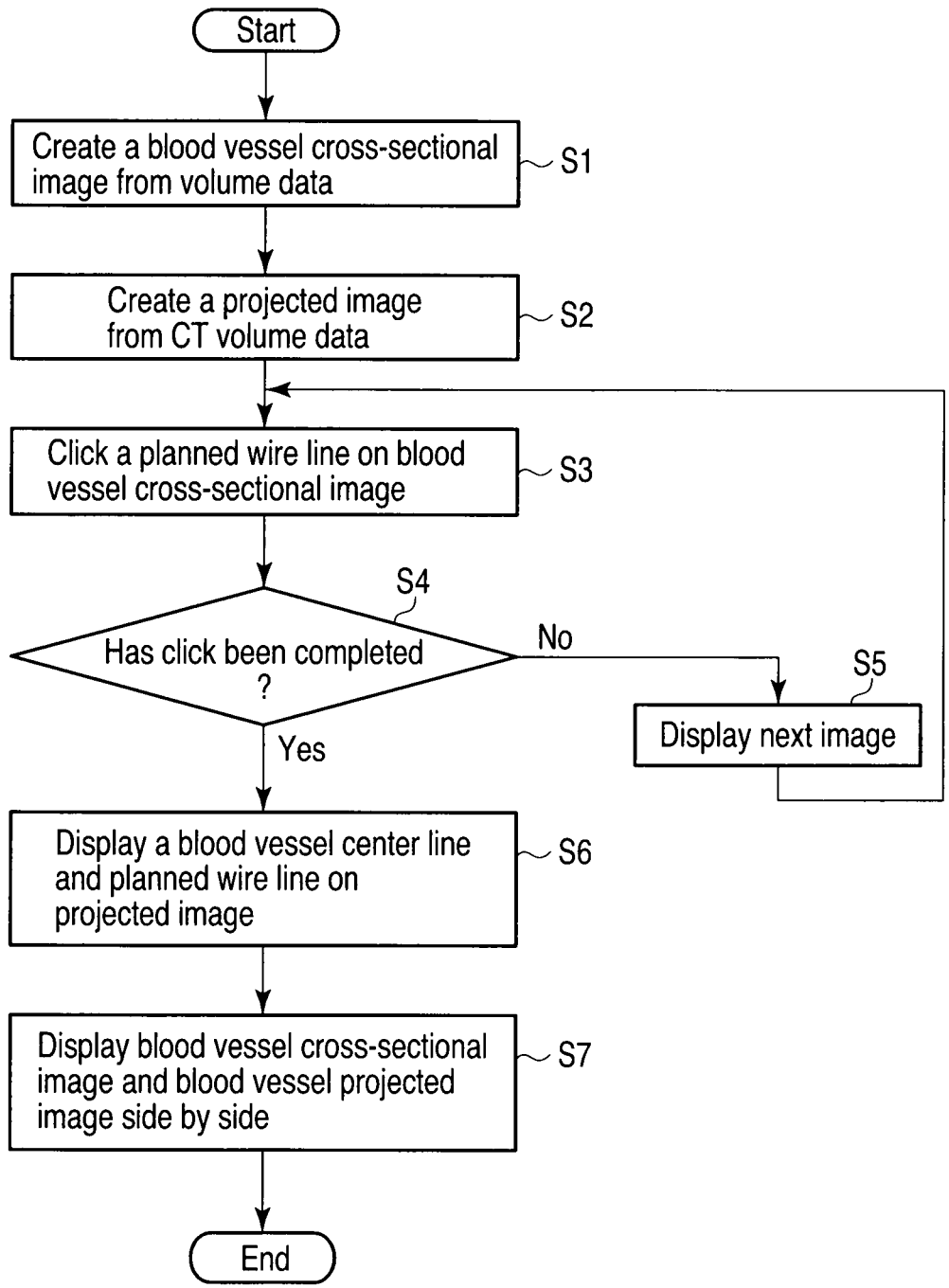
FIG. 3 is a flowchart to help explain the operation of the image display apparatus according to the first embodiment.

First, in step S31, a blood vessel cross-sectional image is created from the CT volume data acquired by the CT volume data acquisition unit 32 as in step S1 of the flowchart of FIG. 3. Next, in step S32, a projected image is created from the CT volume data 50 obtained in step S31 as in step S2 of the flowchart of FIG. 3.

Figure 15:
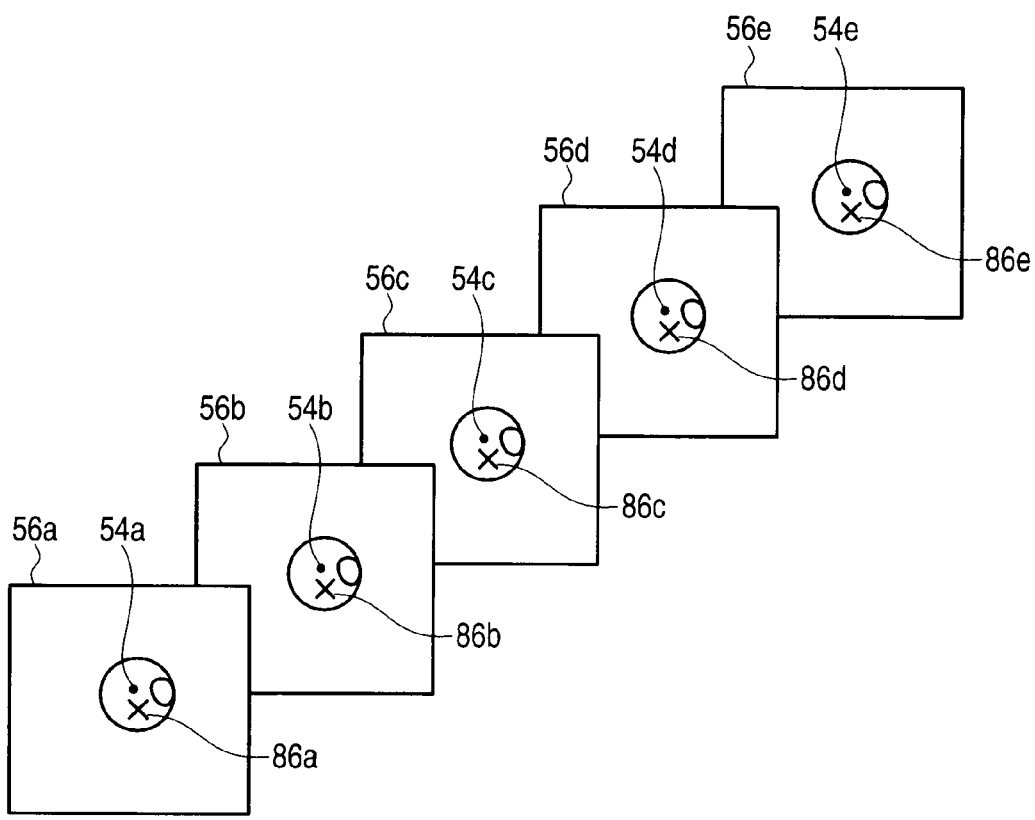
FIG. 15 is a diagram to help explain the operation of the image display apparatus of the second embodiment, showing a plurality of blood vessel cross-sectional images.

Then, in step S33, a part to function as a planned wire line is clicked on a blood vessel cross-sectional image 56. For example, as shown in FIG. 15, the operator clicks an arbitrary point 86c through which the operator wants to pass the wire on a specific one of a plurality of blood vessel cross-sectional images 56a to 56e displayed on the monitor (in this case, a blood vessel cross-sectional image 56c). Then, in step S34, the system control unit 34 calculates a straight line (or a planned wire line) in a three-dimensional space on the assumption that the same two-dimensional coordinates as those of the clicked point 86c have been clicked (at points 86a, 86b, 86d, 86e) for a plurality of images in front of and behind the specific one (in this case, the blood vessel cross-sectional images 56a, 56b, 56d, 56e).

Figures 16A, 16B:
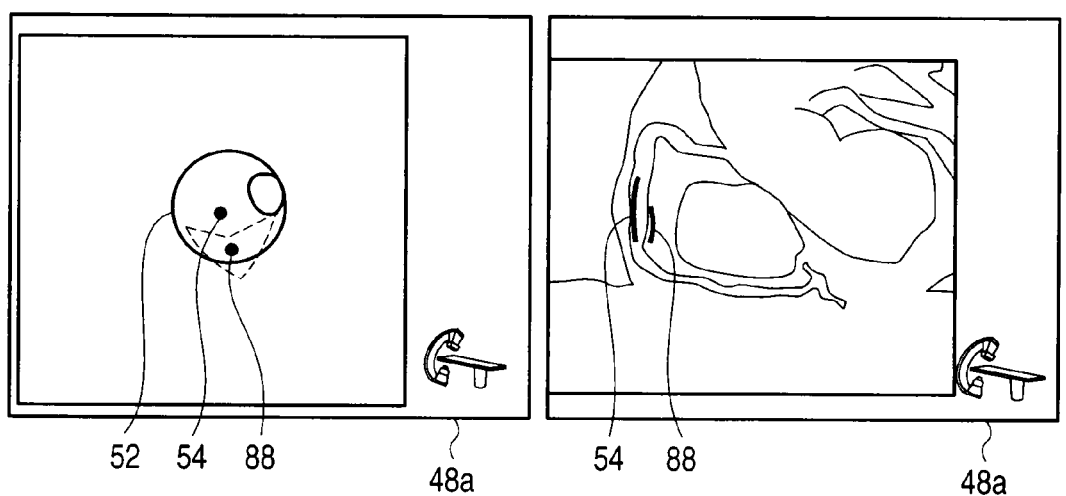
FIGS. 16A and 16B are diagrams to help explain the relationship between a blood vessel cross-sectional image and a projected image in the second embodiment.

Next, in step S35, the blood vessel center line 54 and the planned wire line 88 are displayed on the projected image as shown in FIG. 16B. Then, in step S36, the blood vessel cross-sectional image and the blood vessel projected image are displayed side by side on the screen 48a of the monitor 48.

As described above, even with the second embodiment, the relationship between the blood vessel cross-sectional image and the blood vessel projected image can be displayed in an easy-to-understand manner.

Third Embodiment

Next, a third embodiment of the invention will be explained.

In contrast to the first embodiment, the third embodiment is such that, when a specific point on a projected image is clicked, a line is drawn on a cross-sectional image.

Figure 17:
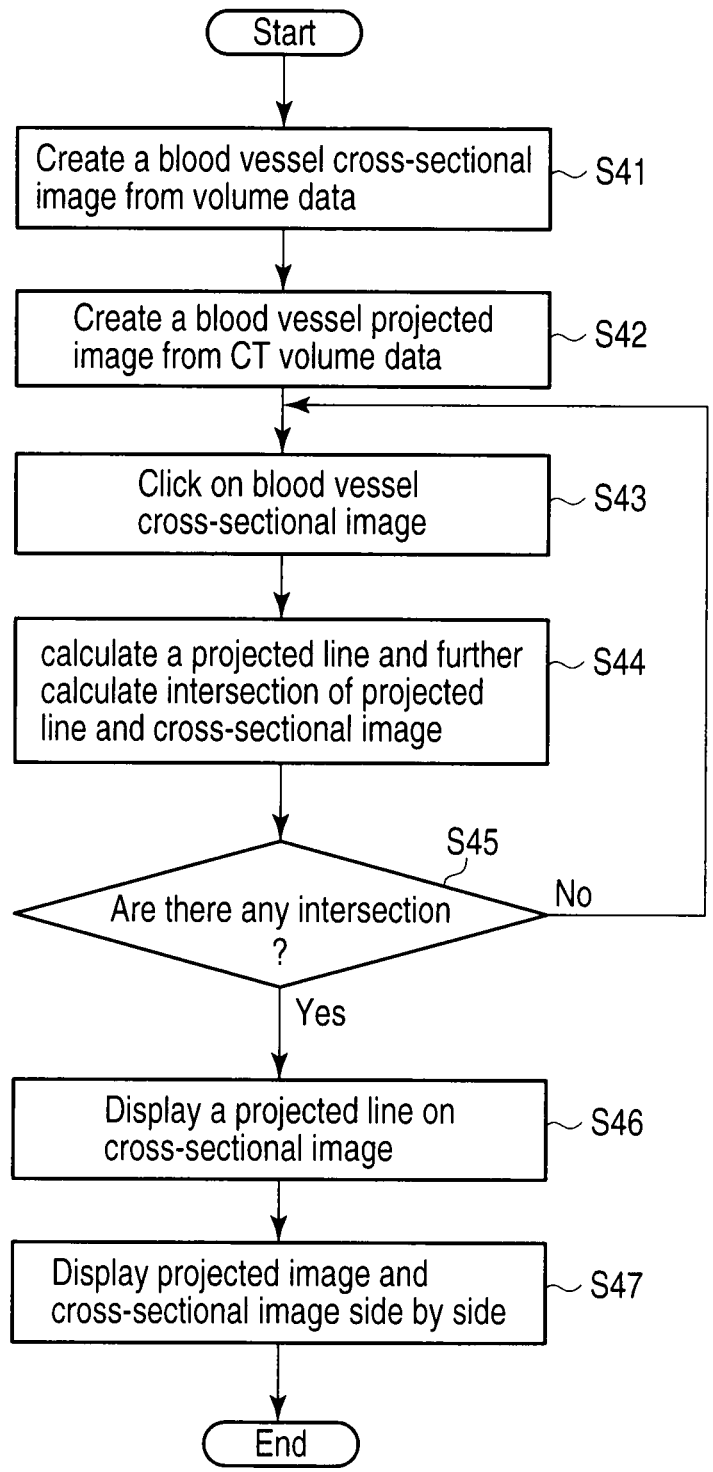
FIG. 17 is a flowchart to help explain the operation of an image display apparatus according to a third embodiment of the invention.

FIG. 17 is a flowchart to help explain the operation of an image display apparatus according to the third embodiment.

First, in step S41, a blood vessel cross-sectional image is created from the CT volume data acquired by the CT volume data acquisition unit 32 as in step S1 of the flowchart of FIG. 3. Next, in step S42, a projected image is created from the CT volume data 50 obtained in step S41 as in step S2 of the flowchart of FIG. 3.

Figure 18:
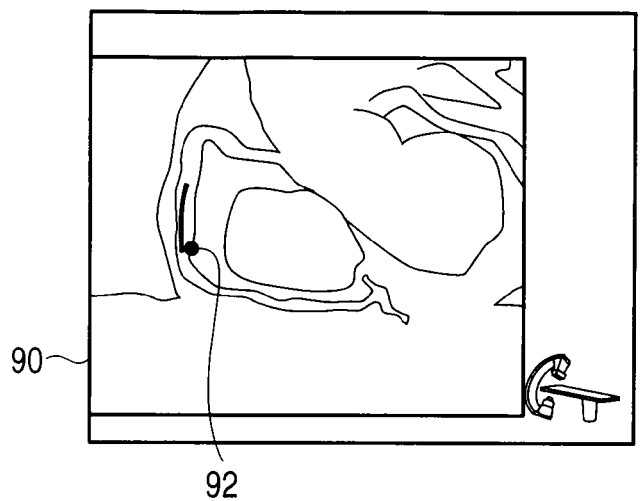
FIG. 18 shows an example of a blood vessel projected image in the third embodiment.
Figure 19:
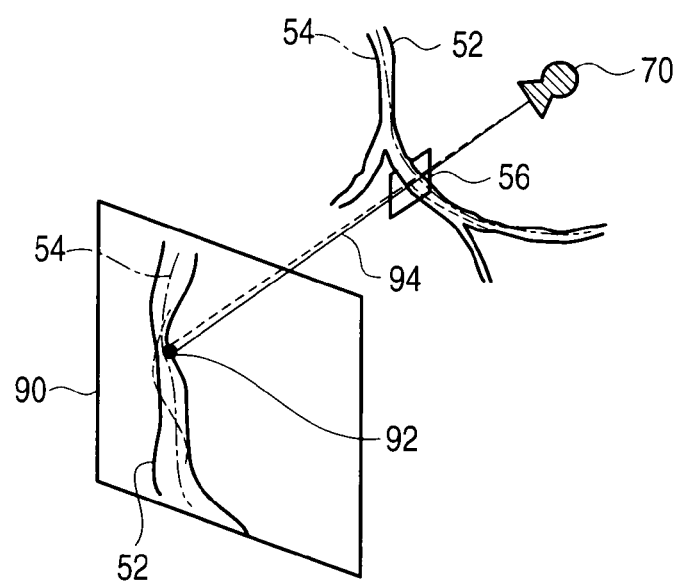
FIG. 19 is a diagram to help explain a three-dimensional geometrical relationship in the third embodiment.

Then, in step S43, one point 92 on a blood vessel projected image 90 is clicked as shown in FIG. 18. Then, in step S44, a projected line is calculated and the intersection of the projected line and the blood vessel cross-sectional image is calculated. For example, as shown in FIG. 19, a line connecting the clicked point 92 and an X-ray source 70 is used as a projected line 94. Then, in step S45, on the basis of the calculation of the projected line 94, it is determined whether the intersection of the projected line and the blood vessel cross-sectional image exists. If there is no intersection, control proceeds to step S43. If the intersection exists, control proceeds to step S46, where the projected line 94 is projected on the blood vessel cross-sectional image 56 as shown in FIG. 20, thereby drawing a line. At this time, a line 96 obtained by projecting the projected line 94 onto the cross-sectional image 56 is also displayed.

Then, in step S47, the blood vessel cross-sectional image and the blood vessel projected image are displayed side by side on the screen 48a of the monitor 48 as shown in FIGS. 21A and 21B.

As described above, even with the third embodiment, the relationship between the blood vessel cross-sectional image and the blood vessel projected image can be displayed in an easy-to-understand manner.

Fourth Embodiment

Next, a fourth embodiment of the invention will be explained.

Each of the first to third embodiments is related to the relationship between a CT projected image and a cross-sectional image. In the first and second embodiments, an example of performing clicking on a CT image and drawing a line on a CT projected image has been explained. In the third embodiment, an example of performing clicking on a CT projected image and drawing a line on a CT image has been explained. However, the invention is not limited to these and may be applied to X-ray images. For instance, in a case where the operator wants to refer to CT images in haste during medical treatment, it is preferable to use X-ray images.

In the fourth embodiment, an explanation will be given about a case where clicking is performed on a CT image and a line is drawn on an X-ray projected image and a case where clicking is performed on an X-ray projected image and a line is drawn on a CT image.

Figure 2B:
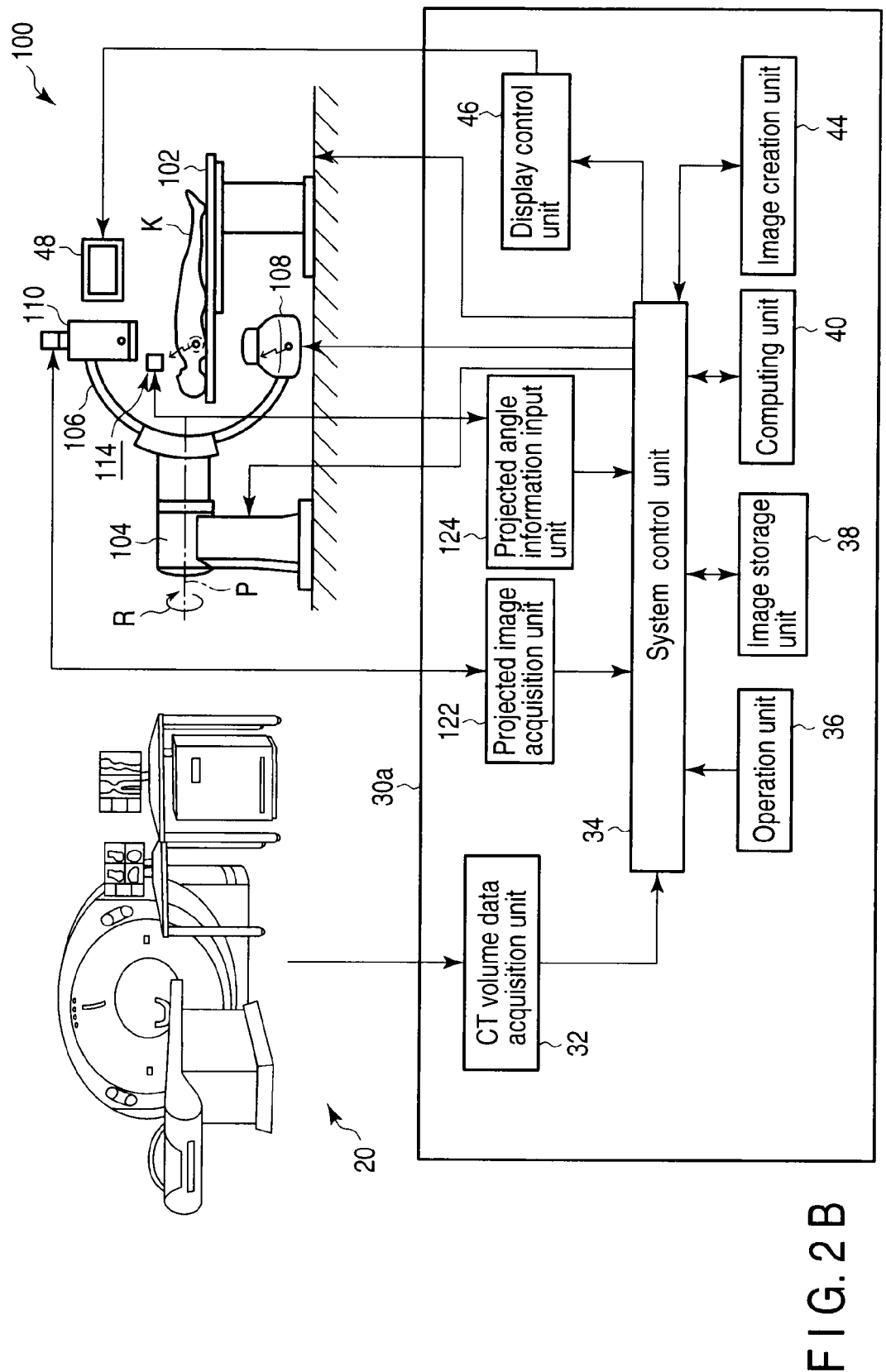

FIG. 2B is a block diagram showing the configuration of an image display apparatus according to the fourth embodiment.

In the fourth embodiment, the same parts as those in the first embodiment are indicated by the same reference numbers and an explanation of them will be omitted. Only what differs from the first embodiment will be explained.

In FIG. 2B, an X-ray diagnostic apparatus 100 comprises a medical table 102 on which a patient (subject) K is laid, a mount 104, a C-arm 106 which is supported by the mount 104 and can rotate in a direction shown by the arrow R, centering on P-axis, an X-ray source 108 which is provided at one end of the C-arm 106, am X-ray detector 110 provided at the other end of the C-arm 106, a monitor 48 which displays a created image, a 3D position detection unit 114 for detecting the position of an instrument, such as a catheter, inserted into the body of patient K, and a control unit 30a which performs cooperative control of these units.

The medical table 102 can be moved in the vertical and horizontal directions and positions the patient K suitably between the X-ray line source 108 and X-ray detector 110.

The C-arm 106 is configured to arrange the X-ray source 108 and X-ray detector 110 so that they may face each other and hold them. The X-ray source 108 includes an X-ray bulb which irradiates the patient K with X-rays and a collimator which collimates the X-rays emitted from the X-ray bulb. The X-ray detector, which is composed of, for example, an image intensifier and an optical system, converts X-ray information passed through the patient K into optical information with the image intensifier and collects the optical information with an optical lens in the optical system. An X-ray planar detector may be used as a detector other than the image intensifier.

The control unit 30a includes not only the CT volume data acquisition unit 32, system control unit 34, operation unit 36, image storage unit 38, computing unit 40, image creation unit 44, and display control unit 46 but also a projected image acquisition unit 122 which acquires projected image data from the X-ray detector 110 and a projected angle information input unit which is for acquiring projected angle information on the X-ray source on the basis of the position information from the 3D position detection unit 114.

With the X-ray diagnostic apparatus 100 configured as described above, an X-ray projected image is obtained via the projected image acquisition unit 122.

Furthermore, the fourth embodiment is based on the assumption that the position adjustment of CT data and X-ray data has been completed. A simple method of the fourth embodiment is to assume that the center of the CT volume data coincides with the rotation center of the supporter for the X-ray imaging system. One known method of improving the accuracy is to obtain projected images of both data and match the images with one another. If the position adjustment of CT data and X-ray data has been completed, then the X-ray projected image has only to be used in place of the CT projected image.

Moreover, in a case where clicking is performed on a CT image and a line is drawn on an X-ray projected image, the same processing operations as in the first and second embodiments are carried out and the fourth embodiment differs from the first and second embodiments only in that a line is drawn on the X-ray projected image instead of drawing a line on the CT projected image.

Furthermore, in a case where clicking is performed on an X-ray projected image and a line is drawn on a CT image, the same processing operation as in the third embodiment is carried out and the fourth embodiment differs from the third embodiment in that clicking is performed on the X-ray projected image instead of on the CT projected image.

Figure 22:
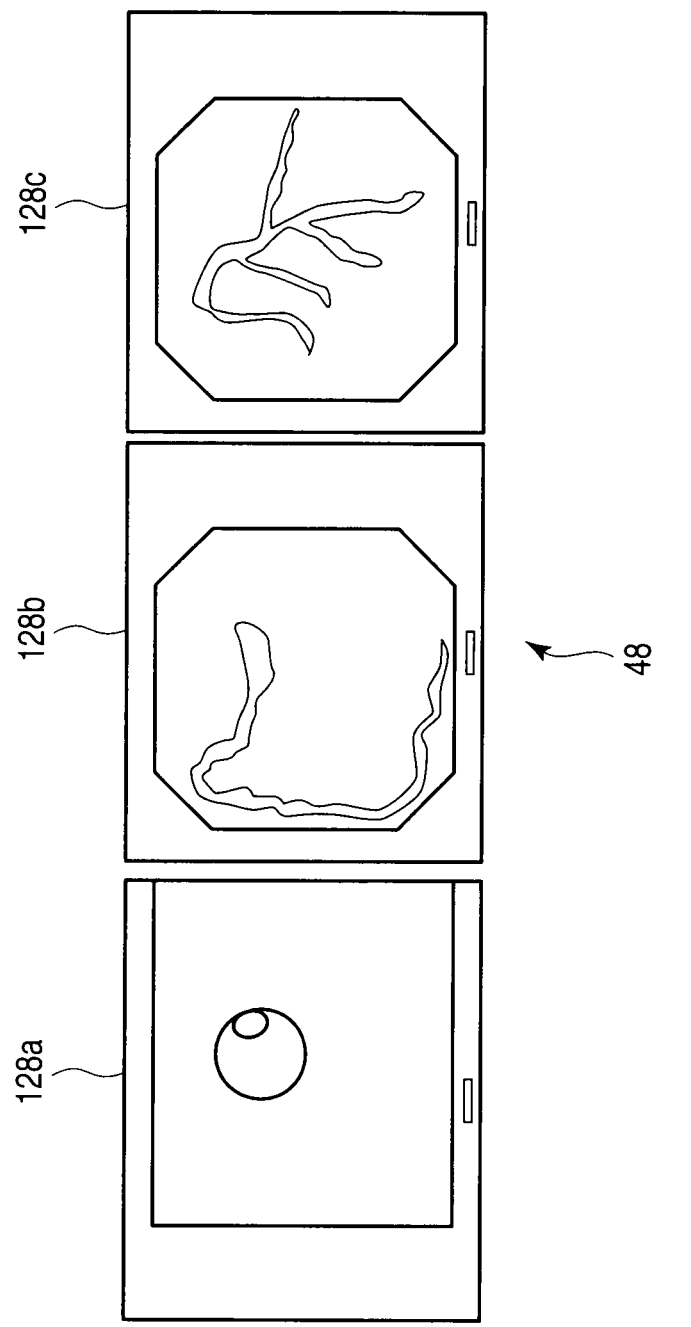
FIG. 22 shows an example of images displayed on a monitor in a fourth embodiment of the invention.

An example displayed on the monitor in this way is shown in FIG. 22. In FIG. 22, a CT blood vessel cross-sectional image 128*a*, an X-ray contrast image 128*b*, and an X-ray transparent image 128*c* are displayed side by side on the monitor.

While in the first to fourth embodiments, a wire route for passing through a complete obstruction has been explained, the invention is not limited to this. For instance, the invention may be applied to a case where the operator wants to check the direction in which plaque has attached.

Furthermore, while in the first to fourth embodiments, CT volume data on blood vessels of the heart has been explained, the invention is not limited to the heart and may be applied to any blood vessel throughout the body. In addition, the invention is not restricted to blood vessels and may be applied to any one of the hollow viscera.

Fifth Embodiment

Next, a fifth embodiment of the invention will be explained.

FIG. 23 is a block diagram showing the configuration of an image display apparatus according to a fifth embodiment of the invention.

In the fifth embodiment, the same parts as those in the first to fourth embodiments are indicated by the same reference numbers and an explanation of them will be omitted. Only what differs from the first to fourth embodiments will be explained.

In FIG. 23, the image display apparatus 30*b* is composed of a CT volume data acquisition unit 32, a system control unit 34, an operation unit 36, an image storage unit 38, a computing unit 40, an image creation unit 44, a display control unit 46, a projected image acquisition unit 122, a projected angle information input unit 124, a storage unit 132, and a supporter control unit 134.

The storage unit 132 is for storing information on the X-ray projected direction of an X-ray diagnostic treatment apparatus 100. The supporter control unit 134 is for controlling the position and angle of the C-arm 106 of the X-ray diagnostic apparatus 100.

The X-ray diagnostic apparatus 100 comprises a medical table 102, a mount 104, a C-arm 106, an X-ray source 108, an X-ray detector 110, a monitor 48, a 3D position detection unit 114, and the image display apparatus.

Next, referring to a flowchart in FIG. 24, the operation of the image display apparatus of the fifth embodiment will be explained.

Figure 25A:
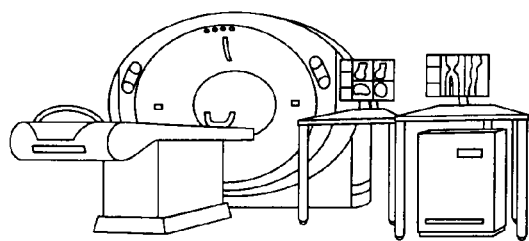
FIGS. 25A to 25C are diagrams to help explain the operation of the image display apparatus of the fifth embodiment, FIG. 25A showing an example of a CT apparatus, FIG. 25B showing an example of volume data, and FIG. 25C showing an example of a blood vessel cross-sectional image.
Figures 25B, 25C:
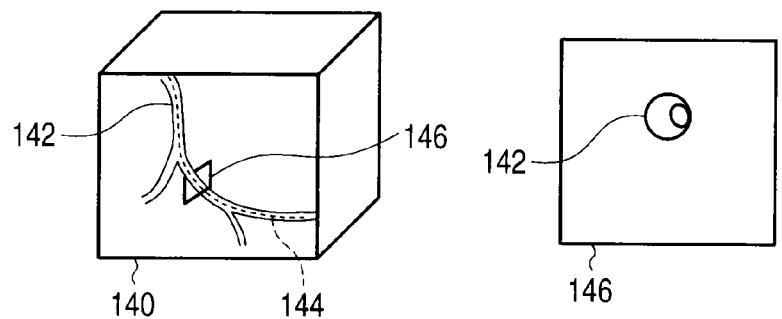

First, in step S51, the CT apparatus 20 creates a blood vessel cross-sectional image from the CT volume data acquired by the CT volume data acquisition unit 32. That is, volume data 140 as shown in FIG. 25B is acquired from the CT apparatus 20 shown in FIG. 25A. Then, the system control unit 34 extracts a blood vessel center line 144 in a blood vessel 142 from the volume data 140. Next, an MPR image perpendicular to the blood vessel center line 144 is created. This is a blood vessel cross-sectional image 146 as shown in FIG. 25C.

Figure 26A:
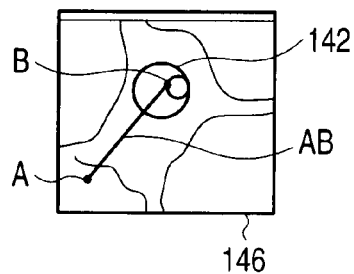
FIGS. 26A and 26B are diagrams to help explain how to calculate a projected direction on a blood vessel cross-sectional image.

Then, in step S52, a projected direction on a blood vessel cross-sectional image is calculated. For example, as shown in FIG. 26A, a certain point A is specified on a blood vessel cross-sectional image 148. Point B functioning as a blood vessel center line on the blood vessel cross-sectional image 146 is found in advance. Then, a straight line AB can be obtained from point A and point B. Although the straight line AB is a two-dimensional straight line on the cross-sectional image, since each of point A and point B has three-dimensional coordinates, the straight line AB can be determined to be a straight line in a three-dimensional space.

Figure 26B:
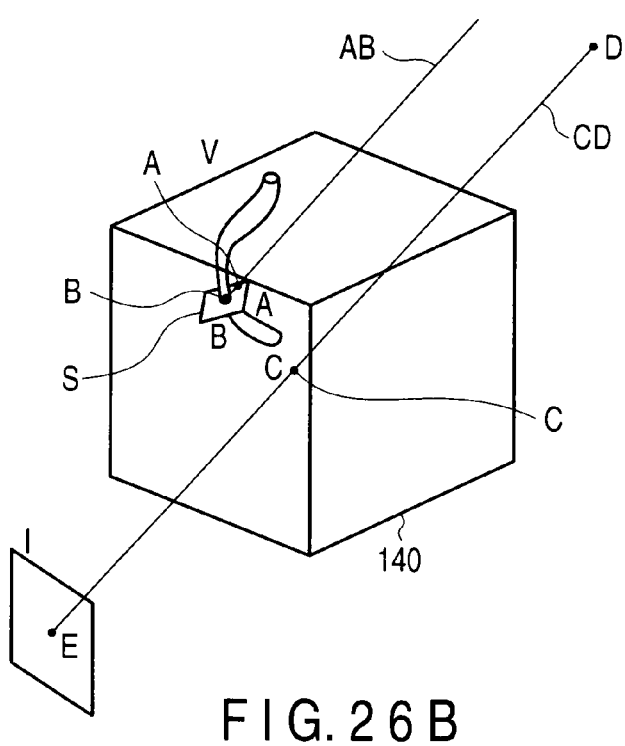

Next, as shown in FIG. 26B, a straight line parallel with the straight line AB and passing through the center point C of the volume data 140 is calculated. Moreover, on the basis of the preset SOD (the distance between the object and the X-ray source: Source-Object Distance), point D functioning as a virtual X-ray source is obtained. Here, the inclination of straight line A and that of straight line B are in the projected direction.

Then, in step S53, the coordinate system is converted. Generally, in the volume data, the X, Y, Z three-dimensional coordinate system is frequently used. In contrast, a coordinate system conventionally used in an X-ray system is frequently represented by an LAO-RAO, CRA-CAU system, with the center of the supporter being zero as shown in FIG. 27. The relationship between them can be converted uniquely, provided that the center of the volume data and the center of the supporter are assumed to be zero. This enables the straight line obtained in step S52 to be represented in the LAO-RAO, CRA-CAU system.

Moreover, in step S54, it is determined whether a projected direction in all directions on the cross-sectional image has been calculated. Here, a projected direction may be calculated at intervals of a specific angle (e.g. 30 degrees). If a projected direction has not been calculated in all directions, control proceeds to step S55, where the cross section S is shifted toward a next projected direction. Thereafter, control proceeds to step S52 and the processes in step S52 to step S54 are repeated.

Figure 29:
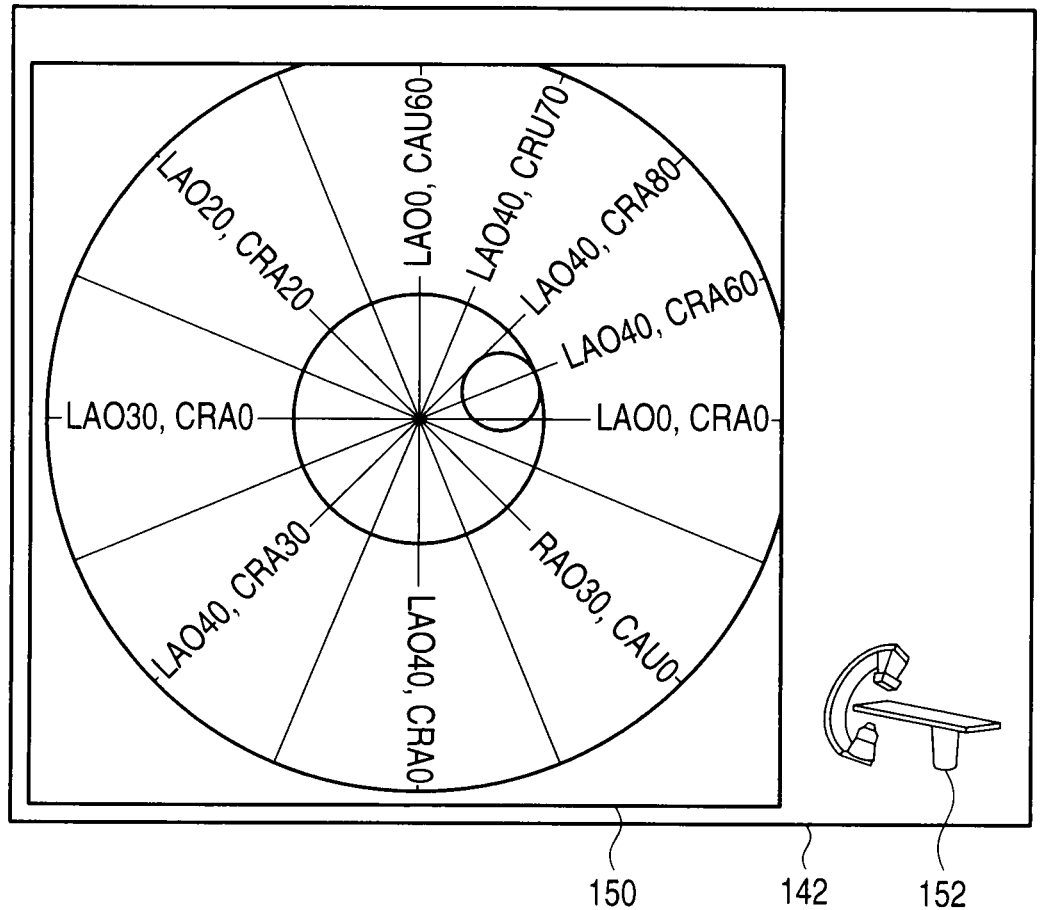
FIG. 29 shows an example of a projected direction in a radiation direction on a cross-sectional image.

In this way, if a projected direction has been calculated for all directions, control proceeds to step S56, where a projected direction in the radiation direction on the cross-sectional image 150 is calculated and displayed as shown in FIG. 29. In FIG. 29, the number attached to each of LAO, RAO, CRA, and CAU represents an angle.

Figure 30:
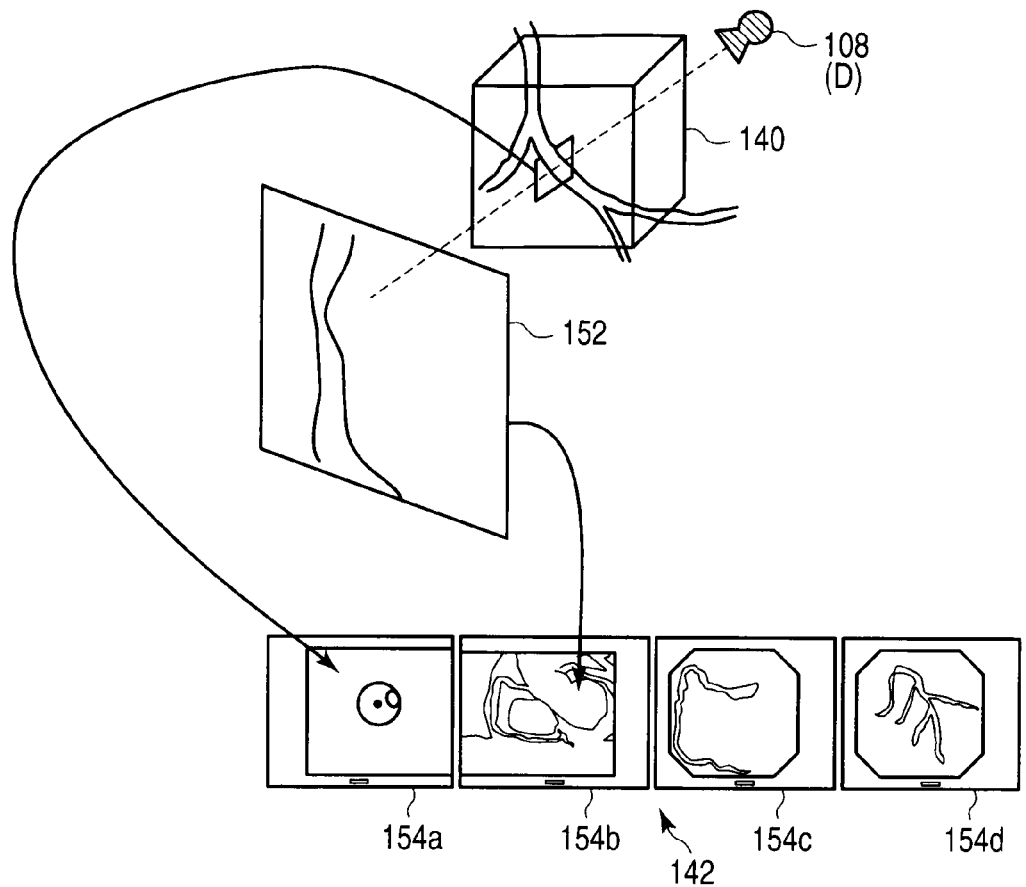
FIG. 30 is a diagram to help explain how to create a projected image.
Figure 31:
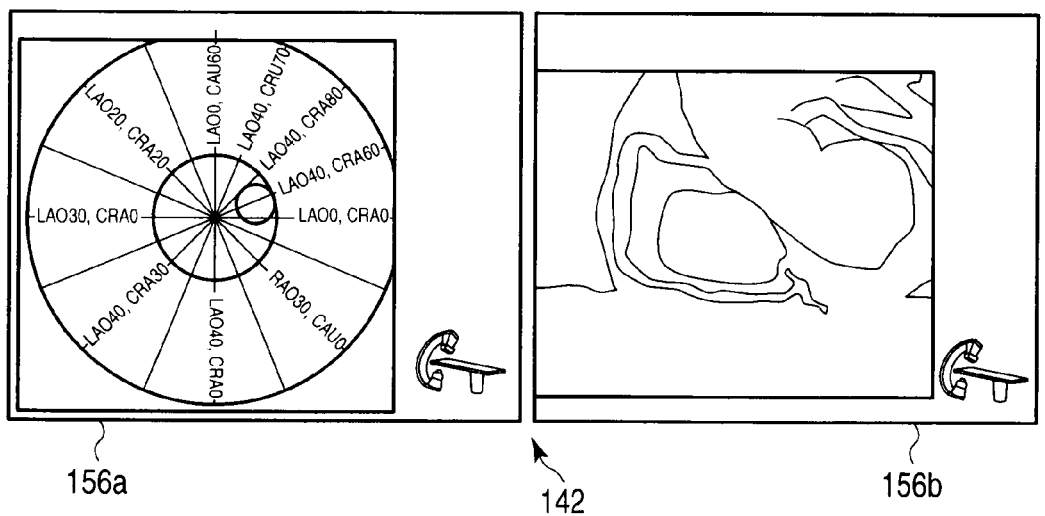
FIG. 31 shows an example of a blood vessel cross-sectional image and a projected image on the image display apparatus according to the fifth embodiment.

Next, in step S57, a projected image is created. As shown in FIG. 30, a CT volume image 140 viewed from point D, the virtual X-ray source, is created as a two-dimensional projected image 152. Thereafter, in step S58, the blood vessel cross-sectional image and the blood vessel projected image are displayed side by side on the monitor 142.

Moreover, for example, as shown in FIG. 30, two or more images may be displayed as are displayed not only a CT blood vessel cross-sectional image 154a and a CT projected image 154b but also an X-ray contrast image 154c and an X-ray transparent image 154d. On the monitor 142, a small-sized image of the X-ray diagnostic treatment apparatus showing the projected direction is displayed together with the cross-sectional image 150.

Then, in step S59, when a radiation direction (e.g., LAO40, CRA0) on the blood vessel cross-sectional image 156a is clicked on the operation unit 136, the angle is selected. The clicking is performed on the mouse, keyboard, or touch panel in the operation unit 36.

Then, in step S60, a CT projected image is rotated by the image creation unit 44 so as to be a projected image viewed from the selected direction and the projected image 156b viewed from the direction is displayed on the monitor 142. If the projected direction of the projected image displayed on the monitor 142 is satisfactory, control proceeds from step S61 to step S62. If not, control proceeds to step S59, where the aforementioned processing operations are repeated.

In step S62, information on the projected direction at the angle is sent to the supporter control unit 134. At the same time, the projected angle information at the time when the projected direction is reached is stored in the storage unit 132 temporarily. Then, in step S63, when the operator presses an operation key (not shown) in the operation unit 36, the C-arm 106 rotates via the supporter control unit 134 according to the angle stored in the storage unit 132.

As described above, with the fifth embodiment, the blood vessel cross-sectional image 156a and the projected image 156b are displayed side by side and clicking on the cross-sectional image causes a projected image in the direction to be displayed, which makes it easier to understand the relationship between the two images. Accordingly, if there is plaque on a blood vessel wall, it becomes easier to understand from which direction the projected image should be viewed to make the plaque easily viewable.

Modification of Fifth Embodiment

Next, a modification of the fifth embodiment will be explained.

In the fifth embodiment, when the radiation direction is clicked on a cross-sectional image, a projected image in the direction is rotated and displayed on the monitor.

In this modification, when clicking is performed on a cross-sectional image, a projected image in the direction is displayed.

Specifically, volume data from which the blood vessel center coordinates have been extracted is used. Since the operator has traced the blood vessel center line after a CT tomography scan in an actual clinical practice, the blood vessel center line data has only to be used directly. If the blood vessel center line has not been extracted from the volume data, specific two points may be clicked on the cross-sectional image.

A method of displaying the radiation direction is to display a color differing from the colors of the other angles if the angle exceeds the rotatable range of the C-arm 106, for example, display the rotatable range in white and an angle exceeding the rotatable range in red. Alternatively, another method is to display nothing if an angle exceeds the rotatable range of the C-arm 106.

Furthermore, the radiation direction specification interface (operation unit 36) does not always have to display images using a radiation pattern as shown in FIG. 29. For example, as shown in FIG. 32A, in the case of a blood vessel 162, an image may be displayed using a combination of a circle 164 and an arrow 166. When the arrow 166 is moved to the direction desired by the operator (e.g., the position of FIG. 32B) on the cross-sectional image 160 by, for example, dragging the mouse on the operator unit 36, a projected image corresponding to this can be displayed.

Moreover, unlike in FIGS. 32A and 32B where the arrow 166 representing the radiation direction is rotated, the cross-sectional image itself may be rotated, with the arrow 166 being fixed, as shown in FIGS. 33A and 33B. In this case, a specific position of the cross-sectional image is dragged with the mouse or the like on the operation unit 36, thereby moving the image.

The created projected image is a projected image of any one of VR, MIP, Ray sum, and slice data on a specific blood vessel.

Sixth Embodiment

Next, a sixth embodiment of the invention will be explained.

In the fifth embodiment, when clicking is performed on a cross-sectional image, a projected image in that direction is displayed. The sixth embodiment is related to a display method of, when a projected image is rotated, drawing a line in the rotation direction on a cross-sectional image.

Figure 34:
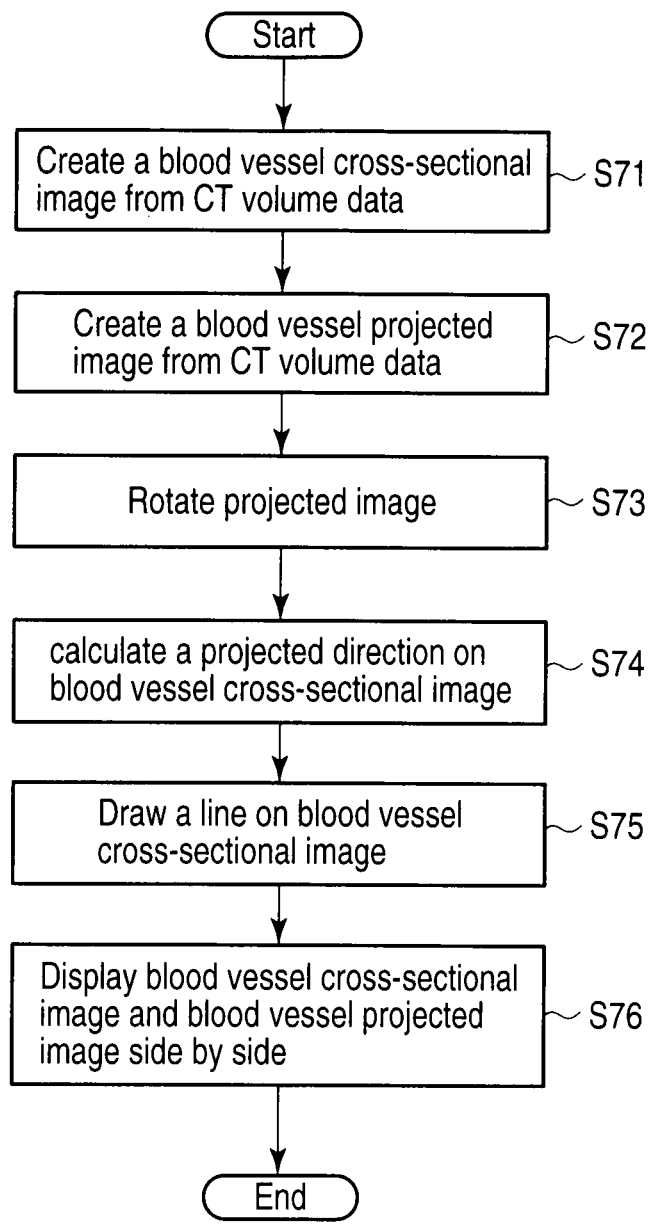
FIG. 34 is a flowchart to help explain the operation of an image display apparatus according to a sixth embodiment of the embodiment.

FIG. 34 is a flowchart to help explain the operation of the image display apparatus of the sixth embodiment.

First, in step S71, the CT apparatus 20 creates a blood vessel cross-sectional image from the CT volume data acquired by the CT volume data acquisition unit 32. Then, in step S72, a projected image is created from the CT volume data. In step S73, the projected image is rotated in a direction desired by the operator. The operations in step S73 and step S74 are the same as displaying general CT images.

Next, in step S74, a projected direction is calculated on the blood vessel cross-sectional image. This is the same as the processing operation of step S52 in the flowchart of FIG. 24. Since the projected direction is determined beforehand in the sixth embodiment, a straight line CD shown in FIG. 26B is determined in advance. Then, a straight line AB parallel with the straight line CD and passing through point B is calculated. In the sixth embodiment, however, the straight line AB scarcely runs on a cross-sectional image and frequently crosses a cross section S. In that case, a straight line AB' obtained by projecting the straight line AB onto the cross section S is calculated.

Figure 35:
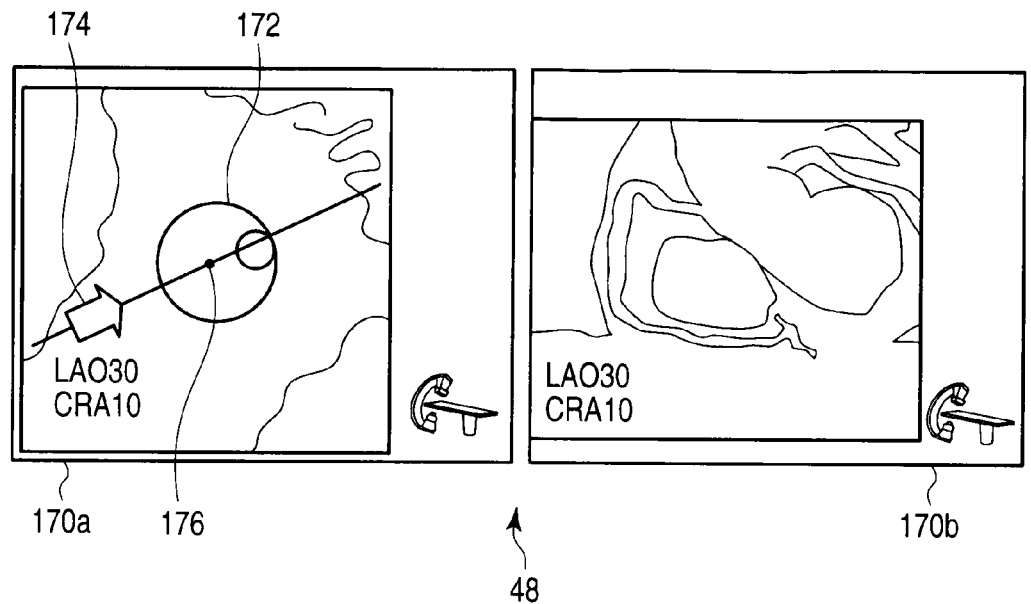
FIG. 35 shows an example of a blood vessel cross-sectional image and a projected image on the image display apparatus according to the sixth embodiment.

In step S75, a line (blood vessel center line) 176 is drawn on the blood vessel cross-sectional image 170a as shown in FIG. 35. In FIG. 35, number 172 indicates a blood vessel and number 174 represents an arrow indicating the projected direction. Thereafter, in step S76, the blood vessel cross-sectional image 170a and the blood vessel projected image 17b are displayed side by side on the monitor 48.

As described above, even with the sixth embodiment, it is possible to display the relationship between a blood vessel cross-sectional image and a blood vessel projected image in an easy-to-understand manner.

Modification of Sixth Embodiment

Next, a modification of the sixth embodiment will be explained.

In the fifth embodiment, when a projected image is rotated, a line in the rotation direction is drawn on a cross-sectional image.

However, instead of a line, a direction may be used on the cross-sectional image.

For example, an arrow may be drawn as in FIGS. 32A and 32B instead of drawing a line on a cross-sectional image. Alternatively, a cross-sectional image may be rotated as shown in FIGS. 33A and 33B instead of drawing a line on the cross-sectional image.

Figures 36A, 36B:
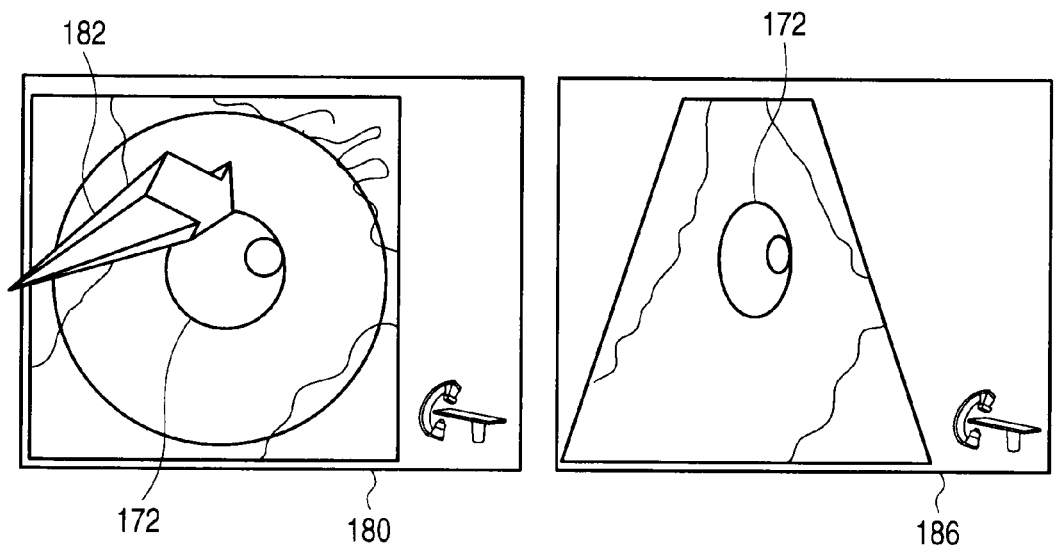
FIGS. 36A and 36B are diagrams to help explain a modification of the fifth embodiment, showing a method of displaying a cross-sectional image.

Moreover, a stereoscopic arrow 182 may be drawn on a cross-sectional image 180 as shown in FIG. 36A instead of drawing a line on a cross-sectional image. In addition, a cross-sectional image 186 itself may be displayed three-dimensionally as shown in FIG. 36B instead of drawing a line on the cross-sectional image.

Furthermore, while in the fifth and sixth embodiments, CT volume data on blood vessels of the heart has been explained, the invention is not limited to the heart and may be applied to any blood vessel throughout the body. In addition, the invention is not restricted to blood vessels and may be applied to any one of the hollow viscera.

The invention is not limited to CT volume data and may be applied to the volume data obtained from an X-ray diagnostic apparatus. Since the volume data obtained from the X-ray diagnostic apparatus can be created during treatment, it is often superior to CT volume data.

Furthermore, the invention is not restricted to CT volume data and may be applied to any 3D data, such as MRI or PET.

It should be noted that the present invention is not limited to the embodiments explained above, and that various modifications may be added without departing from the scope of the present invention.

Furthermore, the above embodiments include different steps of the invention, and thus various inventions can be attained from suitable combinations of disclosed structural elements. As long as the problems mentioned in the Brief Summary of the Invention can be solved and the aforementioned advantages can be attained, the structure may be presented as an invention even if, for instance, some of the structural elements described in the embodiments are omitted or some of the structural elements are combined together.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display apparatus, comprising:
   a volume data acquisition unit which acquires volume data;
   an extraction unit which extracts a tubular object region from the volume data;
   a cross-sectional image creation unit which creates a plurality of cross-sectional images perpendicular to a center line of the extracted tubular object region;
   a projected image creation unit which creates a projected image;
   a display which displays said plurality of cross-sectional images and the projected image;
   a specification unit which specifies a respective arbitrary point on each of the plurality of cross-sectional images displayed on the display; and
   a controller which, according to the arbitrary points specified by the specification unit, superimposes at least two curved lines, including a planned wire line and a center line of the tubular object region, on the projected image on the display, wherein when a blood vessel center line and a planned wire line overlap with each other, the controller is configured to cause the blood vessel center line and the planned wire line to be displayed in such a manner that the blood vessel center line or the planned wire line closer to a viewpoint appears above the blood vessel center line or the planned wire that is farther from the viewpoint.

2. The image display apparatus according to claim 1, wherein the projected image creation unit creates a projected image from the volume data acquired by the volume data acquisition unit.

3. The image display apparatus according to claim 1, wherein the projected image creation unit creates a projected image from X-ray projected data.

4. The image display apparatus according to claim 1, wherein the controller displays a line existing closer to the view point above the other lines on the projected image displayed on the display.

5. The image display apparatus according to claim 1, wherein the controller displays the lines in different colors, different types, or different thicknesses on the projected image displayed on the display.

6. An image display apparatus, comprising:
   a volume data acquisition unit which acquires volume data;
   an extraction unit which extracts a tubular object region from the volume data;
   a cross-sectional image creation unit which creates a plurality of cross-sectional images perpendicular to a center line of the extracted tubular object region;
   a projected image creation unit which creates a projected image from the volume data;
   a display which displays said plurality of cross-sectional images and the projected image;
   a specification unit which specifies a specific point on the projected image displayed on the display; and
   a controller which, according to the specific point specified by the specification unit, displays a line on one of the cross-sectional images displayed on the display, the line being a projected line connecting the specific point and a position of an X-ray source.

7. The image display apparatus according to claim 6, wherein the projected image creation unit creates the projected image from the volume data acquired by the volume data acquisition unit.

8. The image display apparatus according to claim 6, wherein the projected image creation unit creates the projected image from X-ray projected data.

9. The image display apparatus according to claim 6, wherein the controller displays at least two arbitrary points on the one of the cross-sectional images displayed on the display.

10. The image display apparatus according to claim 9, wherein the controller displays the at least two arbitrary points in different colors, different types, or different sizes on the one of the cross-sectional images displayed on the display.

11. An image display apparatus, comprising:
    a volume data acquisition unit which acquires volume data;
    an extraction unit which extracts a tubular object region from the volume data;
    a cross-sectional image creation unit which creates a cross-sectional image perpendicular to a center line of the extracted tubular object region;
    a computing unit which calculates a projected line in a radiation direction on the cross-sectional image created by the cross-sectional image creation unit and calculates a portion of the projected line that intersects the cross-sectional image;

a projected image creation unit which creates a projected image from the volume data acquired by the volume data acquisition unit; and a display which displays the cross-sectional image and the projected image, wherein the display displays the portion of the projected line that intersects the cross-sectional image on the cross-sectional image.

12. The image display apparatus according to claim 11, wherein the display displays radiant lines on the cross-sectional image.

13. The image display apparatus according to claim 11, further comprising a specification unit which specifies a specific point on the cross-sectional image displayed on the display, wherein the display displays a projected image viewed from the specific point specified by the specification unit.

* * * * *